(12) United States Patent
Dallam et al.

(10) Patent No.: US 9,222,257 B2
(45) Date of Patent: Dec. 29, 2015

(54) OPERATING ROOM/INTERVENTION ROOM

(71) Applicant: OR21, LLC, Seattle, WA (US)

(72) Inventors: Richard F. Dallam, Seattle, WA (US); Paul L. Williams, Orange Beach, AL (US); Craig Tagawa, Fairfield, CA (US); Ernest Bates, Napa, CA (US)

(73) Assignee: OR21, LLC, Seattle, WA (US)

( * ) Notice: Subject to any disclaimer, the term of this patent is extended or adjusted under 35 U.S.C. 154(b) by 0 days.

(21) Appl. No.: 14/563,784

(22) Filed: Dec. 8, 2014

(65) Prior Publication Data

US 2015/0159374 A1 Jun. 11, 2015

Related U.S. Application Data

(60) Division of application No. 12/845,673, filed on Jul. 28, 2010, now Pat. No. 8,905,585, which is a continuation-in-part of application No. 11/129,224, filed on May 13, 2005, now Pat. No. 8,112,942.

(60) Provisional application No. 60/570,843, filed on May 13, 2004.

(51) Int. Cl.
*E04B 9/00* (2006.01)
*A61B 19/00* (2006.01)
(Continued)

(52) U.S. Cl.
CPC ............... *E04B 9/006* (2013.01); *A61B 19/26* (2013.01); *A61B 19/5202* (2013.01);
(Continued)

(58) Field of Classification Search
CPC ............ A61G 10/00; A61B 19/26; A61B 2017/00203; E04H 3/08; E04B 9/006; F21V 21/30

USPC ............ 52/79.1, 79.7, 234, 293, 220.1; 454/293; 362/285, 227, 276
See application file for complete search history.

(56) References Cited

U.S. PATENT DOCUMENTS 3,696,805 A 10/1972 Sweeten
3,843,112 A 10/1974 McDonald
(Continued)

FOREIGN PATENT DOCUMENTS

DE 1 434 663 A1 11/1968
DE 40 14 795 C1 2/1992
(Continued)

OTHER PUBLICATIONS

"Automated Guided Vehicle—Description," Swisslog Healthcare Solutions, n.d.,<http://www.swisslog.com/hcs-index/hcs-systems/hcs-agv/hcs-agvcomponents.htm> [retrieved Apr. 22, 2005], 1 page.
(Continued)

*Primary Examiner* — Anabel Ton
(74) *Attorney, Agent, or Firm* — Christensen O'Connor Johnson Kindness PLLC

(57) ABSTRACT

A hospital layout comprising a plurality of adjacent OR/intervention rooms (46, 48) uniquely configured and equipped to perform surgical and other interventional procedures, with adjacent intubation rooms (52) configured and equipped to prepare patients for procedures to occur in the OR/intervention rooms and at least one extubation room (54) adjacent the OR/intervention rooms, configured and equipped to post-intervention awaken and extubate patients. A plurality of universal patient rooms (40) are located adjacent the OR/intervention rooms and universal patient rooms, and are configured and equipped to admit patients for surgery/intervention, prepare patients for surgery/intervention, allow patients to recover post-intervention, and discharge patients post-recovery.

18 Claims, 26 Drawing Sheets

(51) Int. Cl.
  *E04H 3/08* (2006.01)
  *F21S 8/02* (2006.01)
  *F21V 21/30* (2006.01)
  *A61G 10/02* (2006.01)
  *E04B 9/02* (2006.01)
  *A61B 17/00* (2006.01)
  *F21W 131/205* (2006.01)
  *F21Y 101/02* (2006.01)

(52) U.S. Cl.
  CPC ............ *A61G 10/02* (2013.01); *E04B 9/02* (2013.01); *E04H 3/08* (2013.01); *F21S 8/026* (2013.01); *F21V 21/30* (2013.01); *A61B 2017/00203* (2013.01); *A61B 2019/448* (2013.01); *A61B 2019/521* (2013.01); *F21W 2131/205* (2013.01); *F21Y 2101/02* (2013.01)

(56) References Cited

U.S. PATENT DOCUMENTS

| | | | |
|---|---|---|---|
| 4,025,777 A | | 5/1977 | Hayakawa |
| 4,129,122 A | | 12/1978 | Dout |
| 4,359,843 A | | 11/1982 | Schachar |
| 4,571,900 A | | 2/1986 | Kelman |
| 4,678,658 A | | 7/1987 | Casey |
| 4,779,671 A | | 10/1988 | Dolison |
| 4,880,026 A | * | 11/1989 | Ferre et al. ............. 137/234.6 |
| 4,887,196 A | | 12/1989 | Brown |
| 5,038,261 A | | 8/1991 | Kloos |
| 5,093,769 A | | 3/1992 | Luntsford |
| 5,231,981 A | | 8/1993 | Schreiber |
| 5,347,431 A | | 9/1994 | Blackwell |
| 5,383,105 A | | 1/1995 | Agut |
| 5,526,245 A | | 6/1996 | Davis |
| 5,964,065 A | | 10/1999 | Migurski |
| 6,036,337 A | | 3/2000 | Belfor |
| 6,082,799 A | * | 7/2000 | Marek ............. 296/24.38 |
| 6,295,671 B1 | | 10/2001 | Reesby |
| 6,351,866 B1 | | 3/2002 | Bragulla |
| 6,446,287 B2 | | 9/2002 | Borders |
| 6,450,671 B1 | | 9/2002 | Scholz |
| 6,721,976 B2 | | 4/2004 | Schwaegerle |
| 6,880,957 B2 | | 4/2005 | Walters |
| 8,033,686 B2 | | 10/2011 | Recker |
| 8,112,942 B2 | * | 2/2012 | Bohm et al. ............. 52/79.1 |
| 8,905,585 B2 | * | 12/2014 | Dallam et al. ............ 362/276 |
| 2003/0175473 A1 | | 9/2003 | Gillum |
| 2003/0195768 A1 | | 10/2003 | Taylor |
| 2004/0133979 A1 | | 7/2004 | Newkirk |
| 2005/0015878 A1 | | 1/2005 | Bannister |
| 2006/0004605 A1 | | 1/2006 | Donoghue |
| 2011/0015492 A1 | | 1/2011 | Mangiardi |

FOREIGN PATENT DOCUMENTS

| | | |
|---|---|---|
| DE | 200 01 134 U1 | 6/2000 |
| EP | 0 398 079 A1 | 11/1990 |
| EP | 1 657 486 A1 | 5/2006 |
| EP | 2413020 A3 * | 1/2013 |
| WO | 2005/118982 A2 | 12/2005 |

OTHER PUBLICATIONS

Communication Pursuant to Article 94(3) EPC mailed May 16, 2014, in corresponding European Application No. 11 175 781.1, filed Jul. 28, 2011, 5 pages.

Extended European Search report mailed Dec. 3, 2012, in corresponding European Application No. 11 175 781.1, filed Jul. 28, 2011, 8 pages.

International Search Report and Written Opinion mailed Feb. 6, 2006, issued in corresponding International Application No. PCT/US2005/016917, filed May 13, 2005, 17 pages.

"Pyxis HelpMate® SP: Automated Trackless Robotic Courier," CardinalHealth, n.d., <http://www.pyxis.com/ProdDetails.aspx?cid=4&pid=64> [retrieved Apr. 22, 2005], 1 page.

"A Robot to Help Make the Rounds," NASA Scientific and Technical Information (STI), Mar. 22, 2005, <http://www.sti.nasa.gov/tto/spinoff2003/hm_4.html> [retrieved Apr. 22, 2005], 2 pages.

"Robots for the Real World," iRobot®, n.d., <http://www.irobot.com/home.cfm> [retrieved Apr. 22, 2005], 1 page.

* cited by examiner

OPERATING ROOM/INTERVENTION ROOM

CROSS-REFERENCES TO RELATED APPLICATIONS

This application is a division of U.S. application Ser. No. 12/845,673, filed Jul. 28, 2010, which is a continuation-in-part of U.S. application Ser. No. 11/129,224, filed May 13, 2005, now U.S. Pat. No. 7,298,498, which claims the benefit of U.S. Provisional Application No. 60/570,843, filed May 13, 2004, the disclosures of which are all hereby expressly incorporated by reference.

BACKGROUND

The present invention relates generally to hospital/clinical layouts, and more particularly, to the layout, structure and usage of intervention/operating rooms (OR), and related intubation, extubation and patient rooms.

Currently, a patient at a hospital or medical clinic is moved from location to location numerous times in order for a procedure to be completed. Also, typically, OR and intervention rooms and equipment used therein are underutilized in most hospitals and medical facilities, thereby increasing the cost of procedures. In addition, OR/intervention rooms are typically so crowded with equipment, lighting fixtures, booms, monitors, utility columns or booms, hoses, tubes and lines, that it is difficult for OR/intervention room personnel to actually move about efficiently. Also, such equipment can impair the vision of OR/intervention room personnel and impede laminar air flow from an overhead source, over the patient, and then out of the OR/intervention room. Such lighting fixture booms, equipment booms, etc., often set up air eddies or dead spaces. Also, fixtures, equipment, etc., can collect dust particles that can then be blown into the surgical field within the laminar air flow column at the surgical/intervention site thus compromised the laminar air flow system's purpose of reducing surgical/intervention wound infections.

In addition, an extensive period of time is required to clean and prepare an OR/intervention room after a procedure has been completed. The room is manually cleaned, and the soiled equipment, diagnostics, linen, etc., must be removed manually from the room and new supplies, equipment, etc., delivered to the room and set up. This takes time, which reduces throughput and the number of cases per day. The cost of the personnel for carrying out these tasks is not insignificant.

The present invention seeks to address the foregoing drawbacks of existing OR/intervention room structures and procedures. The present invention strives to reduce the number of patient moves, enhance patient safety and provide flexibility and adaptability of the OR/intervention room for future advances in patient care.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

One aspect of the present invention pertains to a plurality of adjacent OR/intervention rooms for performing medical procedures where each room comprises a surgical/intervention zone of a pre-determined area, generally surrounding the location in which the patient is positioned. The surgical/intervention zone is substantially free of monitors, displays, mountings for monitors and displays, overhead utility sources and outlets, equipment booms and mountings, equipment and supply cabinet mountings, as well as equipment, instrument and supply table mountings. The OR/intervention rooms also include an adjustable lighting system incorporated into the ceiling of the room to provide substantially unobstructed light to the surgical/intervention zone. In addition, a ventilation system provides unimpeded laminar flow of air from the ceiling through the surgical/intervention zone.

In an aspect of the present disclosure, the OR/intervention room is constructed with a drop-down ceiling structure that defines a surgery/intervention zone around the patient that is free from articulating arms from monitors, from lighting fixtures, from equipment, and also free from hose drops and utility columns from the ceiling, or other electrical, data, medical gas, vacuum, or evacuation lines, tubes, or cords. The drop-down ceiling can be of a selected size and ideally from about 7 to 8 feet above the floor to establish an unobstructed, sterile zone for the surgery/intervention room.

In a further aspect of the present invention, multiple light sources are recessed in the ceiling of the OR/intervention room and are carried by movable mounting systems that may be aimed, focused, or otherwise controlled as desired by the OR/intervention room personnel. The lighting system may be controlled by microchips mountable on gloves, wristbands, or other articles worn by OR/intervention room personnel, or may be controlled by radio frequency identification tags located on, or incorporated into, instruments used by the OR/intervention room personnel, or may be activated by audio commands.

In another aspect of the present invention, a plurality of large, high resolution audio/video monitors are positioned outside of the intervention zone. Such monitors are configured to provide patient physiological information and digital images, provide communications within and outside of the OR/intervention room, and provide high resolution image guidance for intervention procedures. The content of the monitors may be controlled by a voice-actuated system.

In another aspect of the present invention, movable imaging equipment is shared among the OR/intervention rooms. In this regard, a transportation system is provided for transporting the moving of the mobile imaging equipment among the OR/intervention rooms. Such mobile imaging equipment may include, for example, CT scanners and MRI devices. In addition, the transportation system may include an overhead rail system incorporated into the ceilings of the OR/intervention rooms.

The present invention further comprises intubation rooms adjacent the OR/intervention rooms. The intubation rooms are configured and equipped to prepare patients for procedures to occur in the OR/intervention rooms. Such preparation can take place while the OR/intervention room is being prepared. The present invention also contemplates extubation rooms located adjacent the OR/intervention rooms. The extubation rooms are configured and equipped to post-intervention, awaken, and extubate patients. The OR/intervention room may be cleaned and readied for the next case while the patient would otherwise be awakening in the room.

In accordance with a further aspect of the present invention, the foregoing OR/intervention rooms, intubation rooms and extubation rooms are part of a general hospital layout which also includes a plurality of universal patient rooms located adjacent the OR/intervention rooms. Such universal patient rooms are configured and equipped to admit patients for intervention, prepare patients for intervention, allow patients to recover post-intervention, and discharge patients post-recovery. Such universal patient rooms are adaptable to provide high-level intensive care post-intervention, as well as to function at a lower level in the manner of a traditional patient room, for example, for patient recovery and discharge after relatively minor or routine surgery.

As a further aspect of the present invention, the hospital layout may also include procedural rooms located adjacent the OR/intervention rooms. Such procedural rooms are configured and equipped to share imaging equipment with the OR/intervention rooms. Regular imaging procedures can be carried out at high volume in the procedural rooms. As a consequence, the expensive imaging equipment may be more efficiently utilized than is currently the case.

A further aspect of the present invention includes a novel surgical table, including an articulating platform, pedestal supporting the platform, and a floor-engaging base. The surgical table includes a connection system for connecting the base to a connector hub integrated into the floor of the OR/intervention room, thereby connecting the surgical table to utility outlets for medical gases, electricity, data lines, and cable connectors. In addition, the surgical table includes arm structures at the foot and head of the table, each having outlets or connections for the aforementioned utilities. Such arms are movable between an ergonomically correct position for connection to the utilities of gases, electricity, data, etc., and then movable to a position below the top surface of the table platform so as to be retracted out of the way. The outlet arms at the head or foot of the table permit the sterile surgical drape over the sides of the table to be undisturbed during a procedure.

In a further aspect of the present invention, an anesthesia machine is detachably dockable to the base of the surgical table. The anesthesia machine has a connection system for connecting the anesthesia machine to the connector hub integrated into the floor of the OR/intervention room and also for connecting the anesthesia machine to the surgical table for utilities, communications, control cables, etc. A control system for controlling the anesthesia machine may be at a remote location so that several patients may be monitored at the same time.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
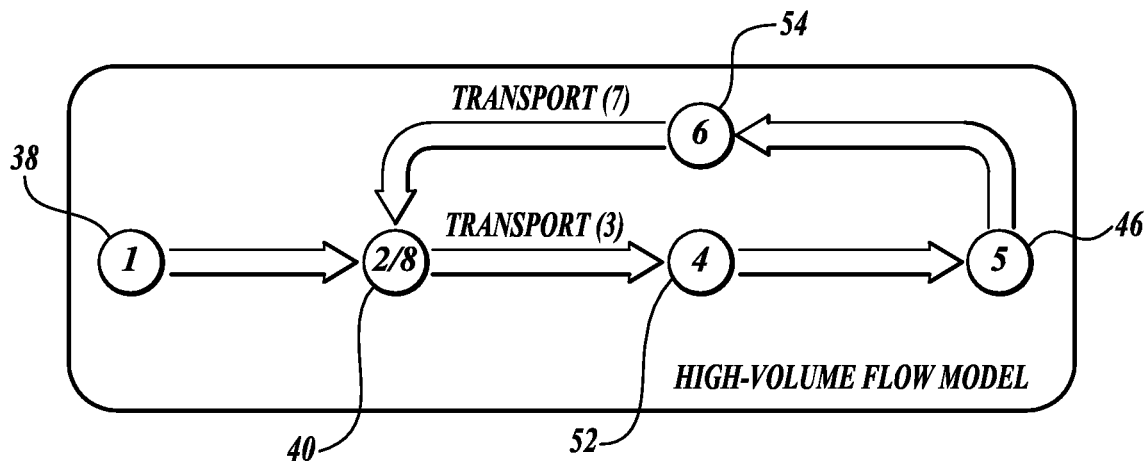
FIG. 1 is a schematic view of patient flow when utilizing a high volume OR/intervention room of the present invention.
Figure 2:
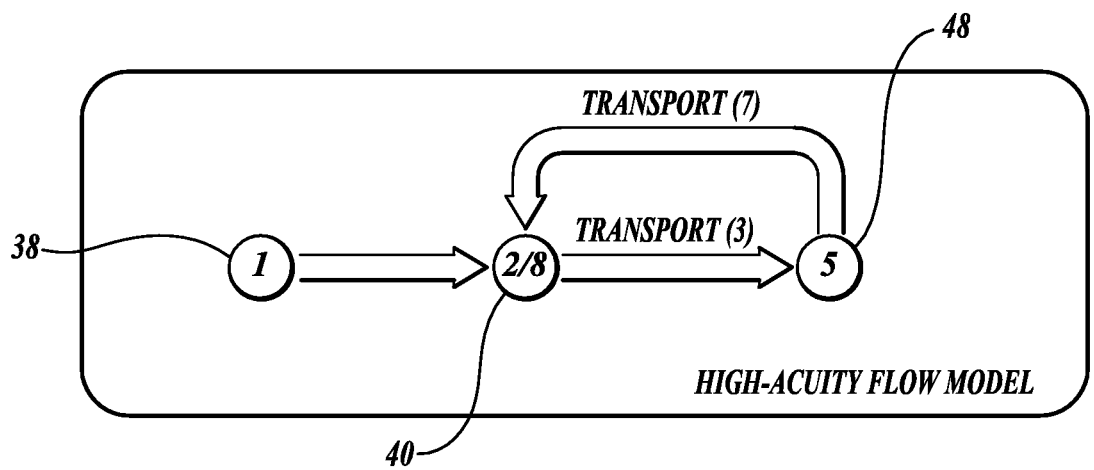
FIG. 2 is a schematic diagram of patient flow utilizing a high-acuity OR/intervention room of the present invention.

FIGS. 1 and 2 schematically illustrate patient flow utilizing the present invention. These figures will be discussed more fully below.

Figure 3:
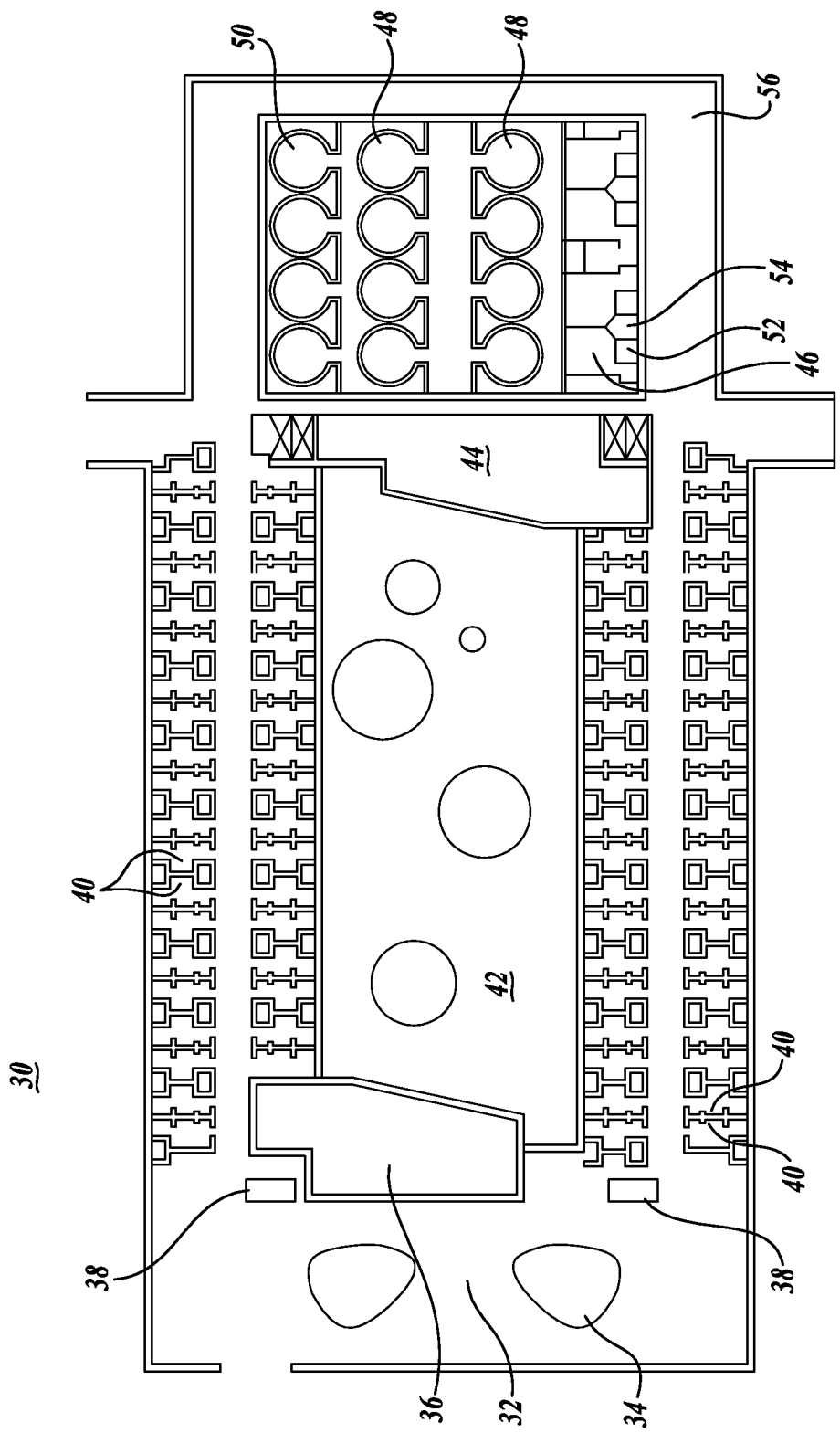
FIG. 3 is a schematic layout of a hospital or clinical setting in accordance with the present invention.

Next, referring to FIG. 3, a hospital layout 30, in accordance with one embodiment of the present invention, is illustrated. The layout includes a lobby area 32, a portion of which may be occupied by a retail sub-area 34 offering flowers, gifts, toiletries, and other products, as in a typical hospital. Public/family support area 36 is adjacent to the lobby. In this area, family members can meet with hospital personnel to discuss/conduct administrative matters and consult regarding procedures being carried out or to be carried out. Also, waiting areas and restrooms may be provided. Concierge stations 38 are also located in the lobby adjacent to universal patient rooms 40 that are arranged in two rows on the opposite side of a center courtyard 42. A nursing support area 44 is located at the opposite end of the courtyard from the public/family support area 36. Nursing stations, a lounge, lockers, and other facilities for medical staff are in the support area 44.

A series of high volume intervention or operating rooms 46 and a series of high-acuity intervention or operating rooms 48 are located adjacent the nursing support area 44. A series of imaging procedural rooms 50 are located adjacent or between the OR/intervention rooms 46 and 48 to create imaging suites. As discussed more fully below, the imaging procedural rooms and OR/intervention rooms share CT, MRI, and other imaging equipment. OR/intervention room Intubation rooms 52, as well as extubation rooms 54, are located adjacent to the high volume OR/intervention rooms 46. A corridor 56 extends around the OR/intervention rooms and the intubation and extubation rooms and between rows of patient rooms 540. The structure and use of universal patient rooms 40, high volume OR/intervention rooms 46, and corresponding intubation and extubation rooms 52 and 54 and high-acuity OR/intervention rooms 48 are described in further detail.

Figure 4:
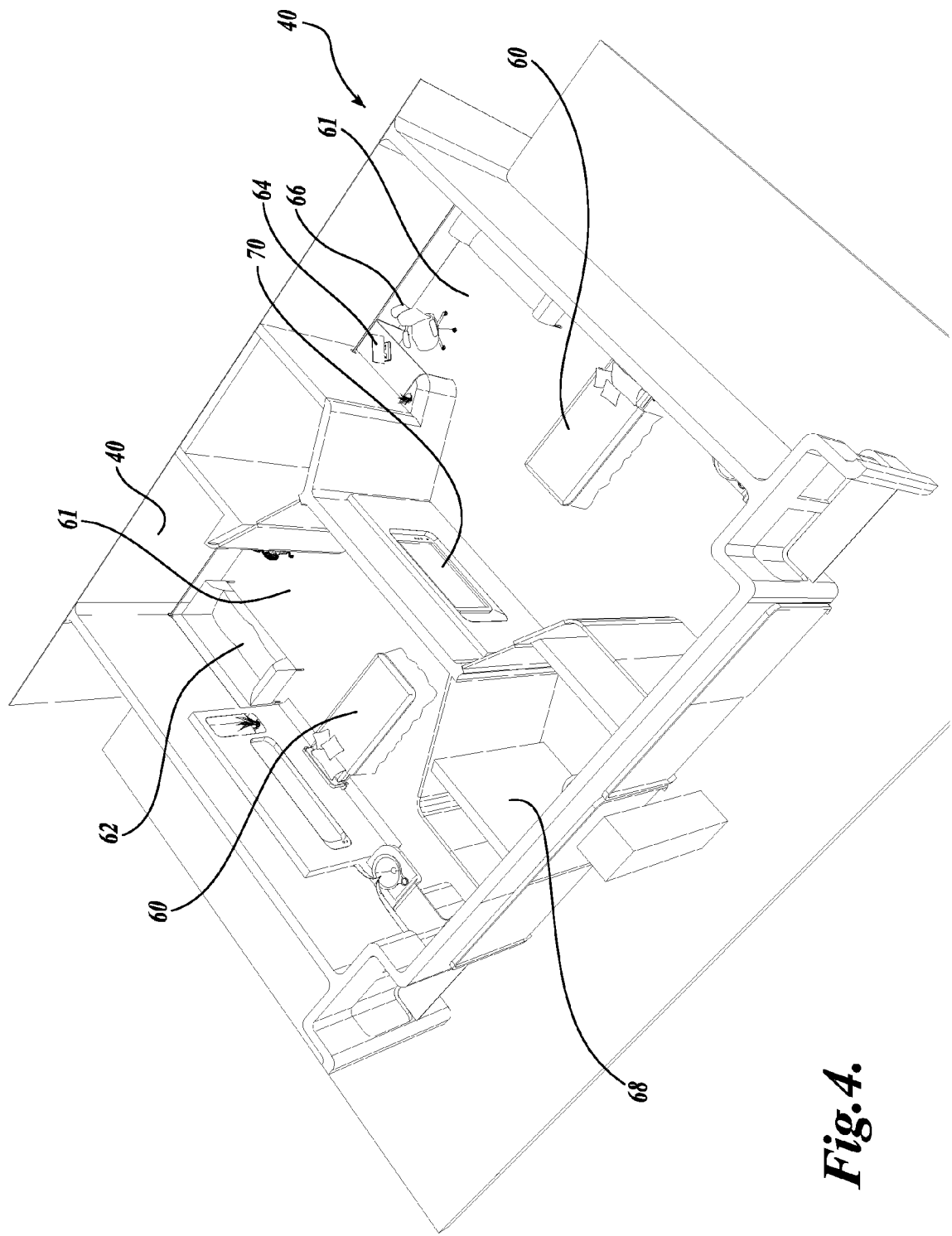
FIG. 4 is a perspective view of universal patient rooms in accordance with the present invention.

FIG. 4 illustrates two universal patient rooms 40, positioned side by side. Such patient rooms are located closely adjacent to the OR/intervention rooms 46 and 48 and are designed to eliminate several separate rooms or stations currently used for patient care between admission and discharge. Patients are initially met at the concierge station 38 and then taken directly to the universal patient rooms 40 for admission and preparation prior to the surgical/intervention procedure. From the patient room 40, the patient is taken either to an intubation room 52 or directly to a high-acuity OR/intervention room 48. Family members may be with the patient in rooms 40.

As shown in FIG. 4, the patient rooms 40 may include a bed 60 and a lounge area 61 furnished with a couch 62 or other types of seating furniture for the patient or family members. The rooms 40 are also configured with a desk surface 64 and desk chair 66 for use by the patient and/or family members. Toilet and bathing facilities 68 are provided for each of the universal patient rooms. A large screen monitor 70 is provided to display applicable physiological data of the patient being monitored, as well as to serve as a patient television for education, ordering of meals, and entertainment.

As noted above, patients are taken from universal patient rooms 40 directly to an intubation room immediately prior to a procedure to be performed in a high volume OR/intervention room 46, or directly to a high acuity OR/intervention room 48. After the procedure is completed, patients are returned directly to the universal room 40 from either the high-acuity OR/intervention room 48 or a high volume OR/intervention room 46, or via an extubation room 54. In the universal patient room 40, the patient is reunited with family members after an initial recovery period (Stage I Recovery) The patient remains in the universal patient room 40 during the recovery period and until discharged. The patient may be discharged directly from the universal patient room 40, rather than having to be transported to a separate inpatient bed unit or discharge station/area.

The use of the universal patient room 40 reduces the number of patient transports needed, thereby enhancing not only patient safety and reduced anxiety, but also operation efficiency, as well as reduction of potential medical errors. As a result, the satisfaction of both patients and medical staff is increased. To meet these goals, the universal patient rooms need to be "acuity adaptable." In other words, the patient rooms must be able to accommodate a variety of activities, from an intensive care level, after an organ transplant, to a more traditional patient room, for example, for a patient recovering from surgery for a broken arm. The patient room is capable of accommodating the equipment and monitoring devices needed for intensive patient care.

Figure 5:
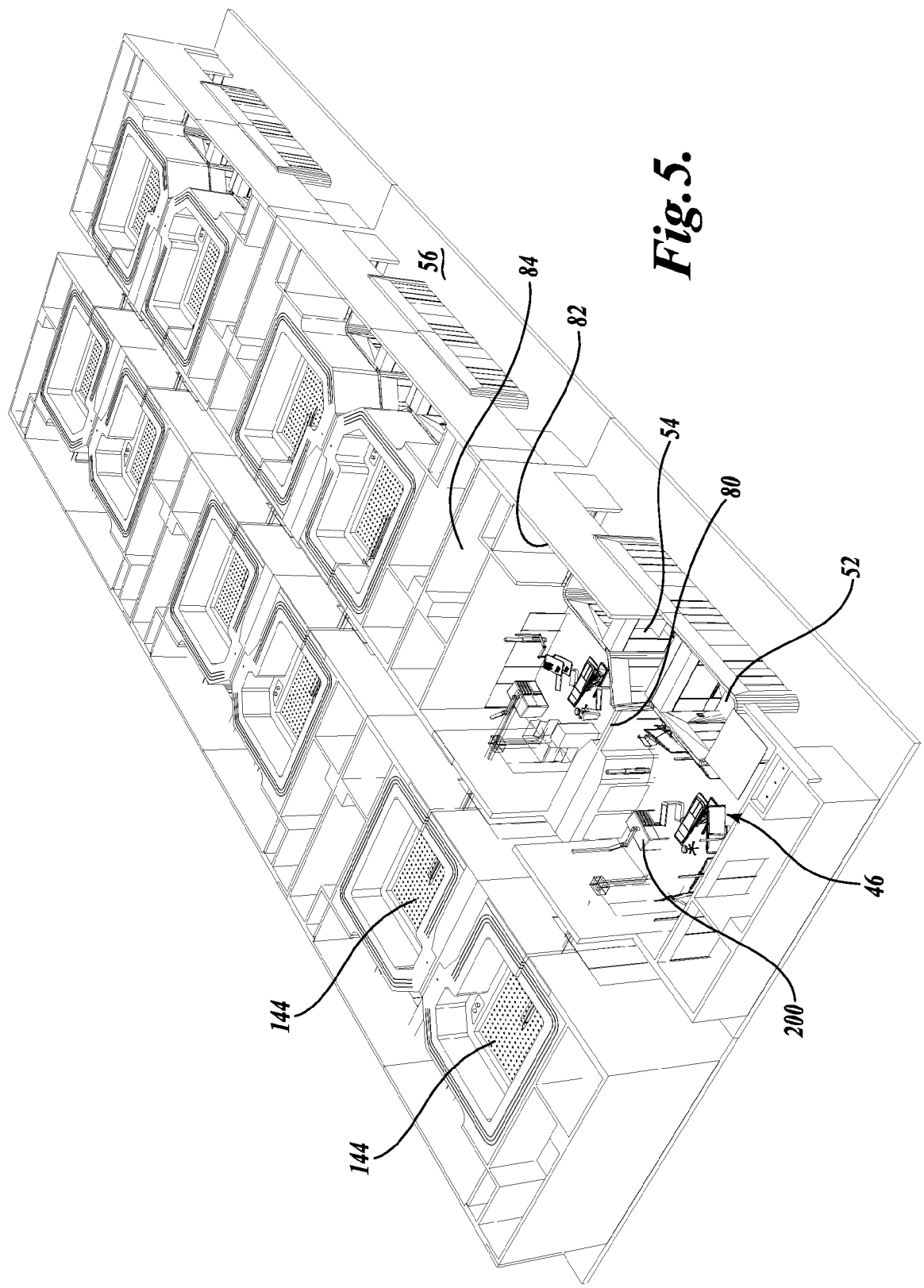
FIG. 5 is a perspective view of several high volume OR/intervention rooms with adjacent intubation and extubation rooms in accordance with the present invention.

Next, the high volume OR/intervention rooms 46 and associated intubation rooms 52 and extubation rooms 54 will be described with reference to FIGS. 5-10. FIG. 5 illustrates a series of high volume OR/intervention rooms 46 positioned in side-by-side pairs and separated by a common wall 80. As also shown in FIG. 5, a singular extubation room 54 is positioned at the end of common wall 80 to serve both of the two OR/intervention rooms 46. An intubation room 52 is located on opposite sides of the extubation room 54 so as to be adjacent a corresponding OR/intervention room 46. A scrubbing station 82 may be located along each side of the intubation rooms 52 opposite the extubation room 54. Also an equipment room 84 may be located between adjacent sets of OR/intervention rooms 46. Of course, rooms for other purposes may also be positioned between the sets of OR/intervention rooms 46.

Figure 6:
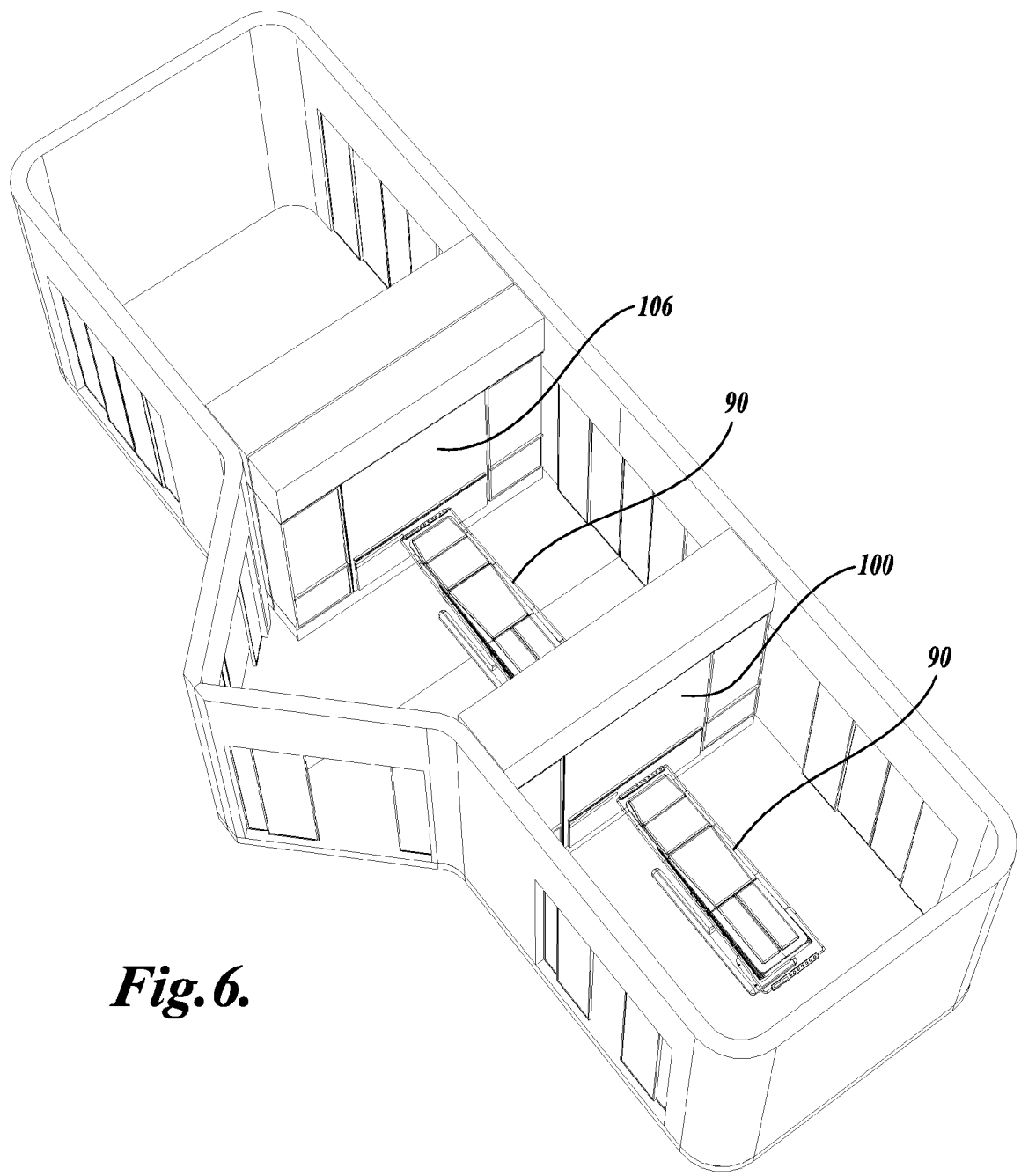
FIG. 6 is a perspective view of an extubation room flanked by intubation rooms on either side in accordance with the present invention.

Next, referring to FIG. 6, one extubation room 54 is illustrated as positioned between two intubation rooms 52. As described above, the extubation room 54 is shared by two adjacent OR/intervention rooms 46. Some of the activities/tasks currently carried out in the OR/intervention room are instead performed in the intubation and extubation rooms 52 and 54. A patient is prepped and induced in the intubation room while the previous procedure is being completed in the OR/intervention room and while the OR/intervention room is being cleaned and prepared for the patient. In this regard, the intubation room, as noted above, is located directly adjacent an OR/intervention room. Also in the intubation room, the patient is placed on a surgical table 90, which is then simply rolled into the adjacent OR/intervention room and used during the procedure. As discussed more fully below, the surgical table includes an anesthesia unit 92 that docks to the surgical table and remains with the table until the patient has been extubated after the procedure. The patient is anesthetized in the intubation room so that the procedure may begin immediately upon the patient being moved to the OR/intervention room.

Figure 7:
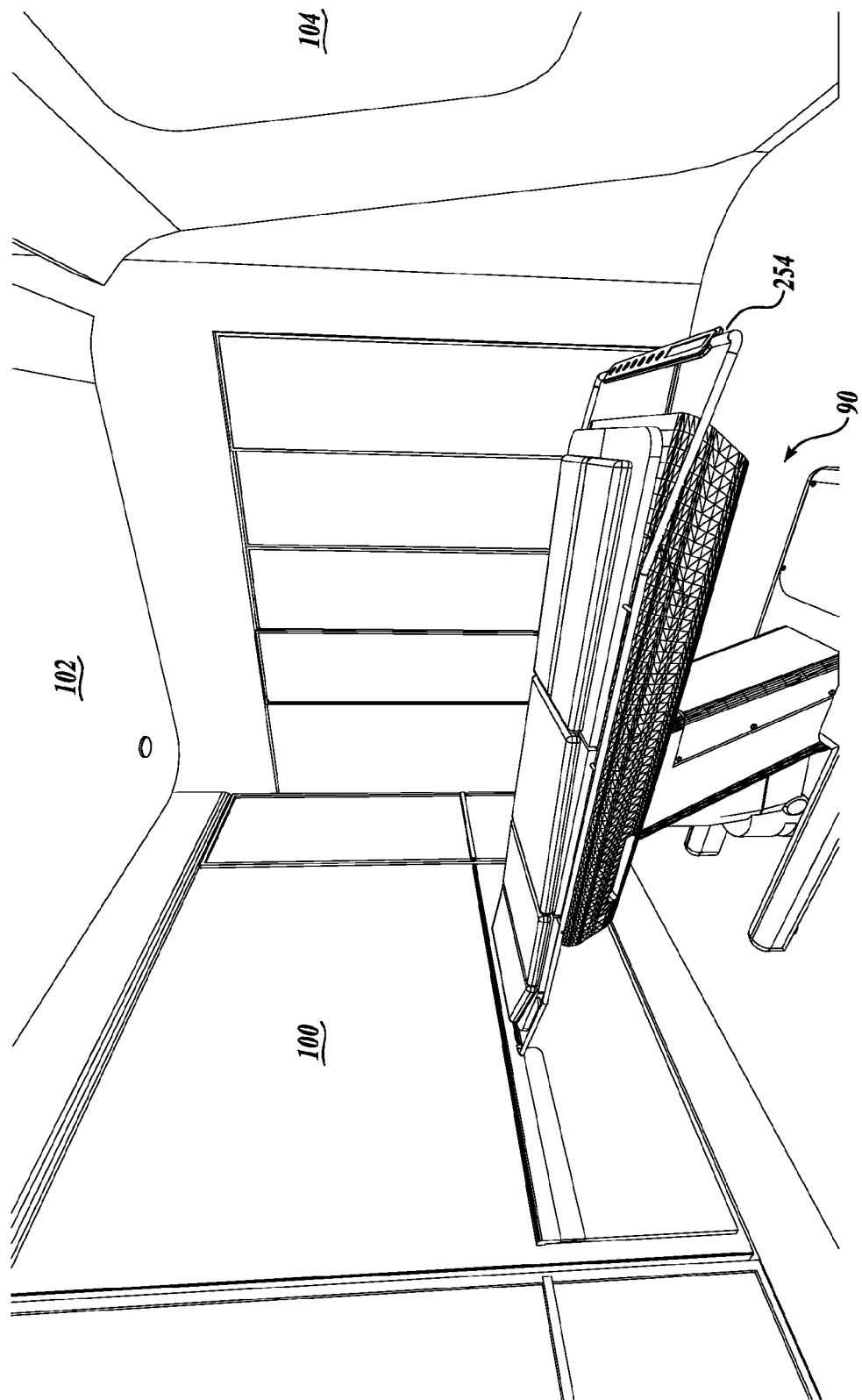
FIG. 7 is a partial perspective view of a portion of an intubation room.

As shown in FIG. 7, the OR/intervention room may include a large wall screen display 100 on which the patient's physiological condition, including vitals, can be displayed in large format. Also, digital X-rays, the results of prior CT scans, or MRIs can be shown on the screen display 100. The intubation room may include other screens, for example, the ceiling 102 of the room can display various scenes, for instance the sky, even the condition of the actual sky outside of the hospital clinic. Another wall 104 of the intubation room may display a television screen or a video screen for the comfort and/or distraction of the patient. Once the patient has been prepared and the OR/intervention room has been turned over, the patient is moved directly into the OR/intervention room for the start of the procedure.

After the procedure has been completed, the patient is immediately moved to the extubation room to be awakened and extubated. This allows the OR/intervention room to be immediately cleaned and readied for the next patient. As a consequence, the OR/intervention room can be used for more procedures than in a conventional or existing hospital or clinic, especially when the OR/intervention room is being used for interventions of less than about two hours duration. Such interventions may include, for example, orthopedic, general, urological, ENT, ophthalmological or plastic procedures.

As in the OR/intervention room, the extubation room may include a large format screen display on one of the walls 106 of the room to display the physiological condition of the patient. Also, the room is equipped to provide medical cases, fluids, medication, etc., to the patient. In the room, the patient may be lying on the same surgical table previously used in the OR/intervention room and the intubation room. This reduces having to move the patient from a procedure surface to a recovery surface and then a transport surface.

From the extubation room, the patient is returned to the same room 40 where the patient was admitted. The patient will recover and remain in the same room 40 until discharged.

Figure 8:
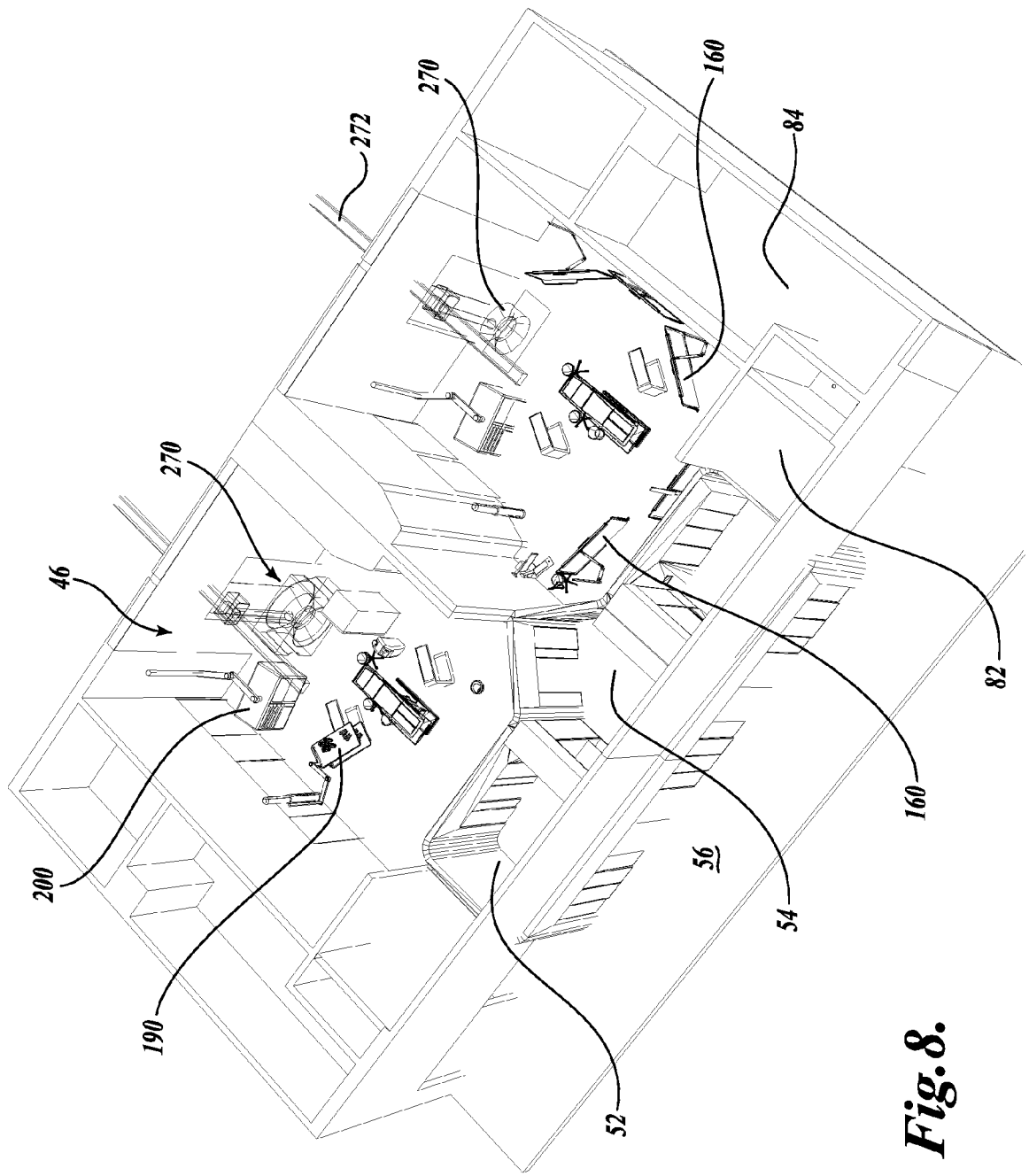
FIG. 8 is a perspective view of two side-by-side high-volume OR/intervention rooms.
Figure 9:
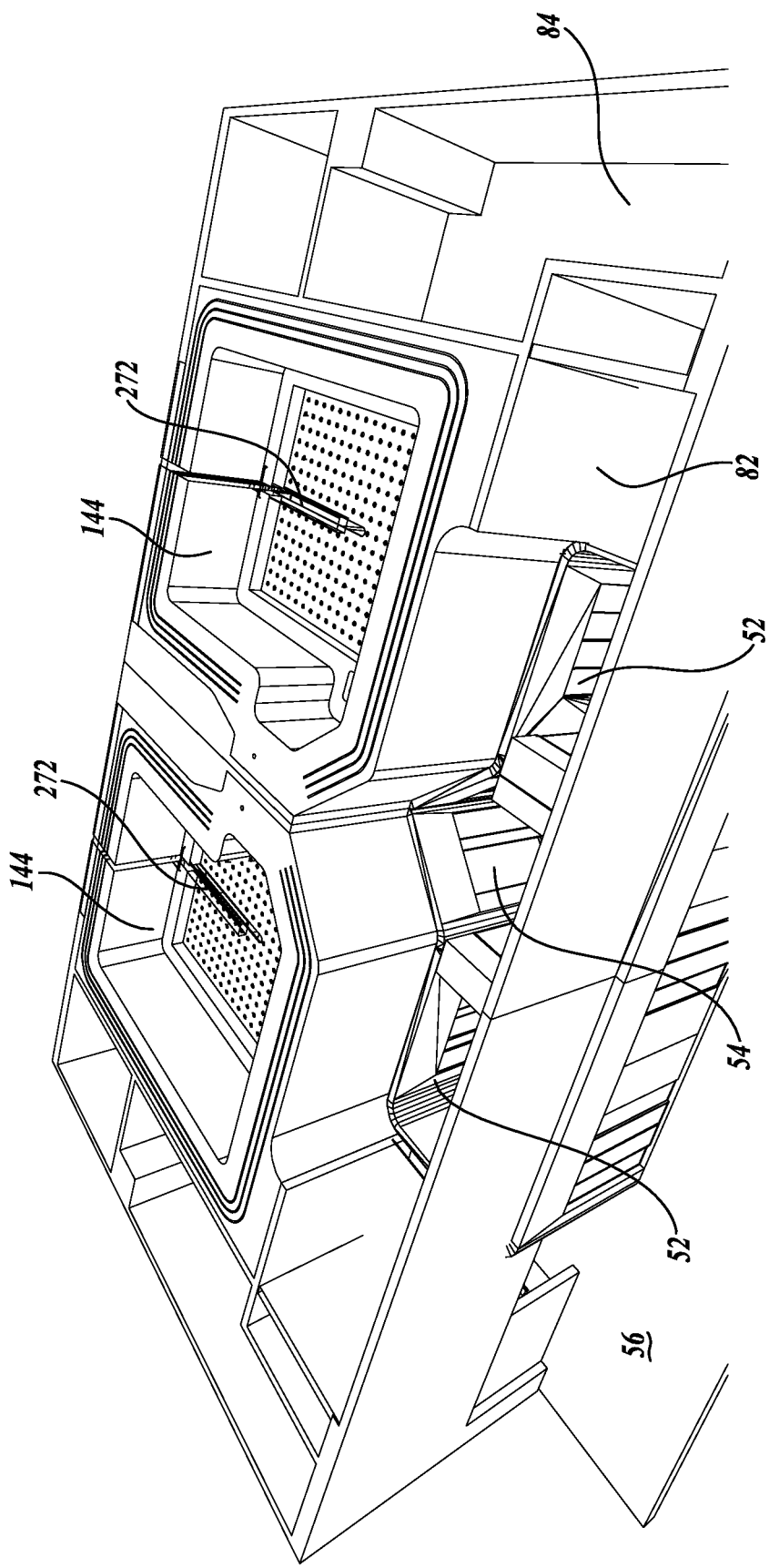
FIG. 9 is a perspective view of the area above the OR/intervention rooms of FIG. 8.

The OR/intervention room 46 will now be described with reference to FIGS. 8, 9, and 10, 10A and 10B. As shown in FIGS. 8 and 9, two OR/intervention rooms 46 are located side-by-side. This enables the two OR/intervention rooms to share an extubation room 54. However, more than two OR/intervention rooms may be positioned side-by-side to each other.

One severe problem with current OR/intervention rooms is that there is so much equipment, tables, booms, cords, and tubes leading to and from the patient and monitors, devices, etc., that mobility around the patient may be very difficult, and in fact dangerous. The present invention establishes a surgery/intervention zone of a defined size around the patient that is free from articulating arms for monitors, lighting, equipment, etc., free from hose drops and utility columns from the ceiling, or other electrical, data, medical gases, vacuum, or evacuation lines, tubes, and cords. Such surgery/intervention zone may be of a select size, for example, a 20-foot diameter. This establishes an unobstructed sterile zone for the surgery/intervention team to freely and efficiently function within.

Figure 10:
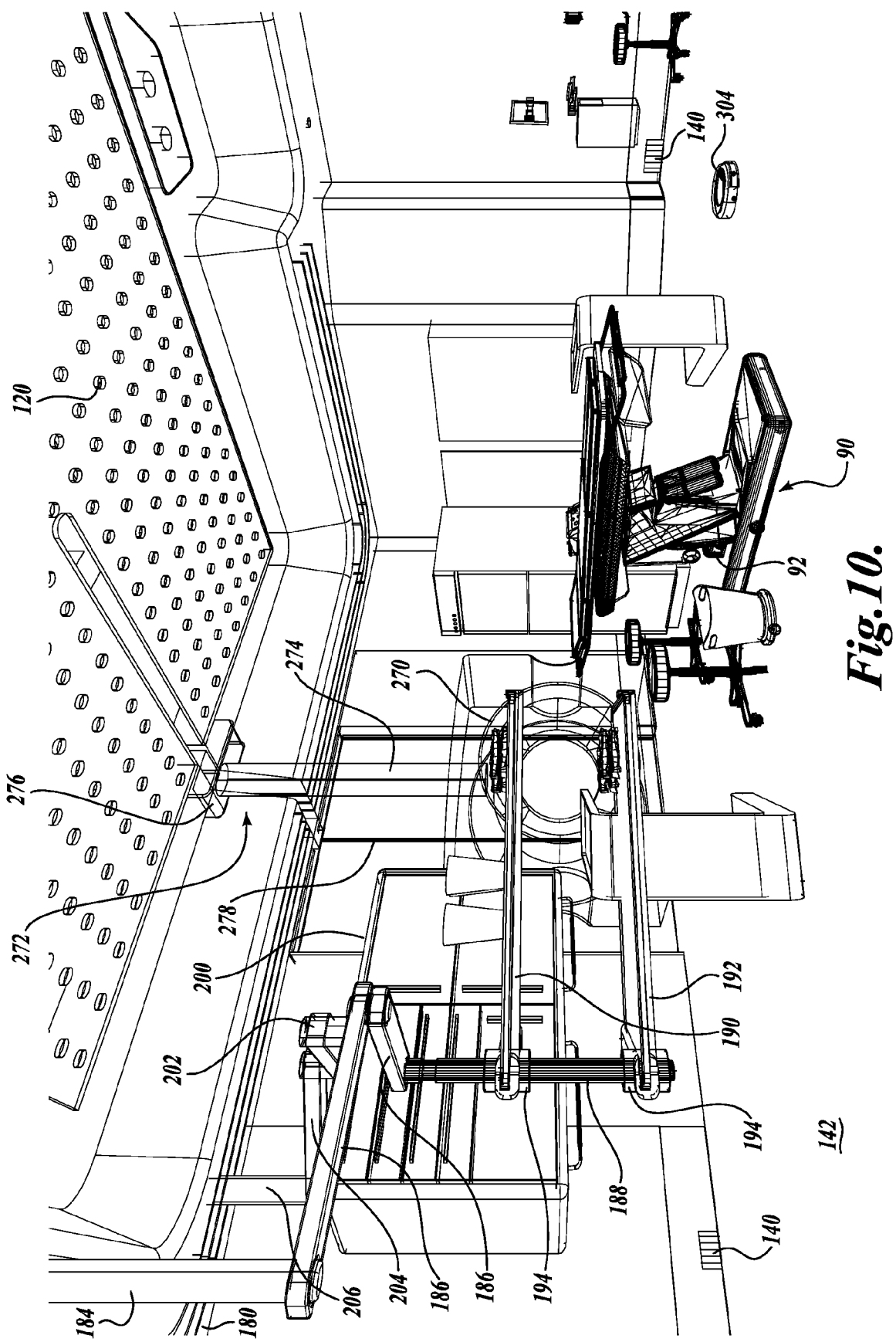
FIG. 10 is a perspective view of a portion of the OR/intervention room of FIG. 8.
Figure 10A:
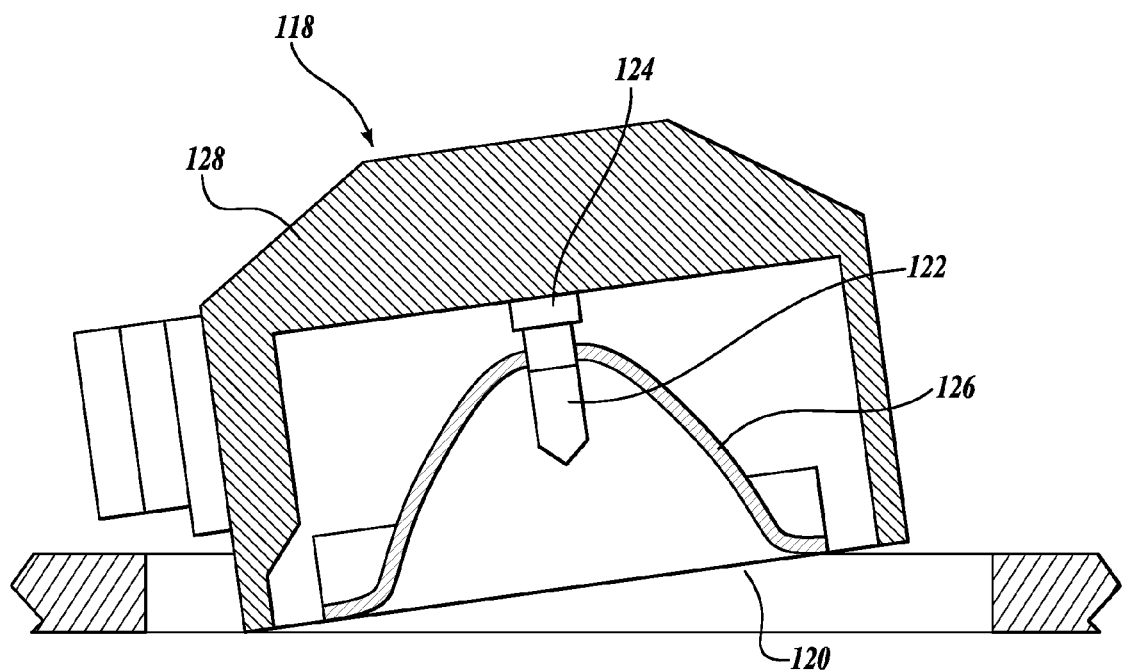
FIG. 10A is a fragmentary elevational view of a ceiling light of the present invention.
Figure 10B:
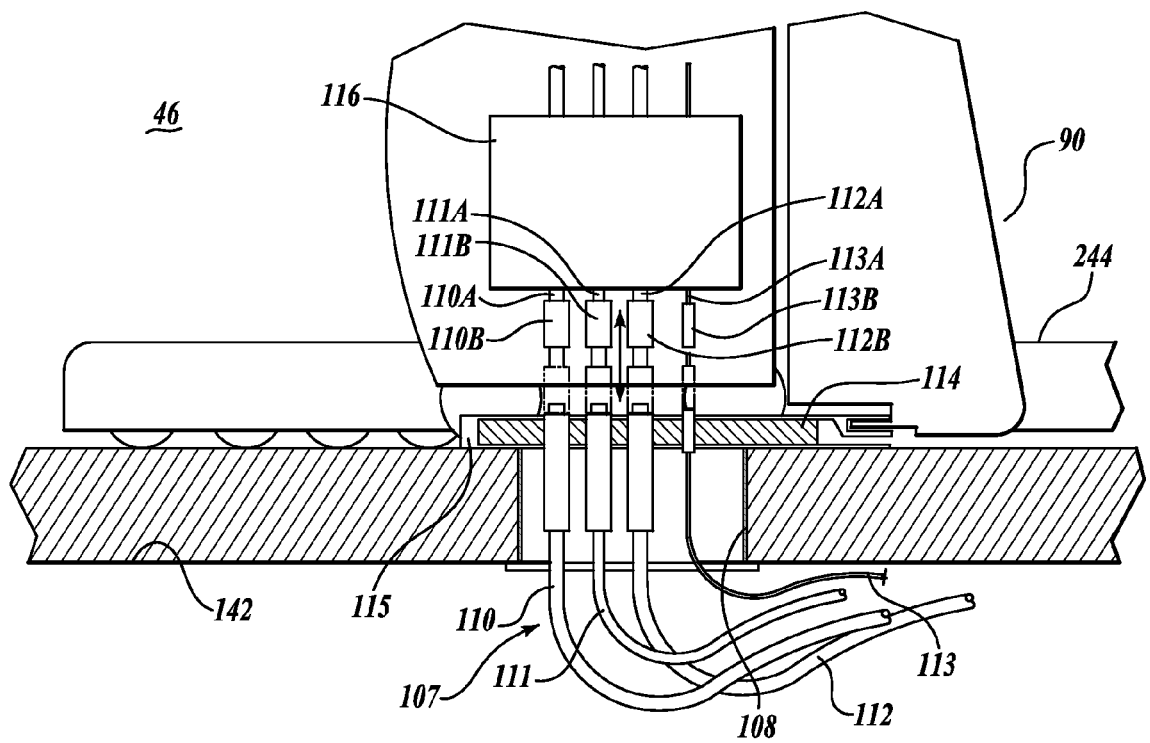
FIG. 10B is a fragmentary elevational view of a connector hub to supply medical gases, vacuum source, electricity, data, and other utilities to the OR/intervention room.
Figure 11:
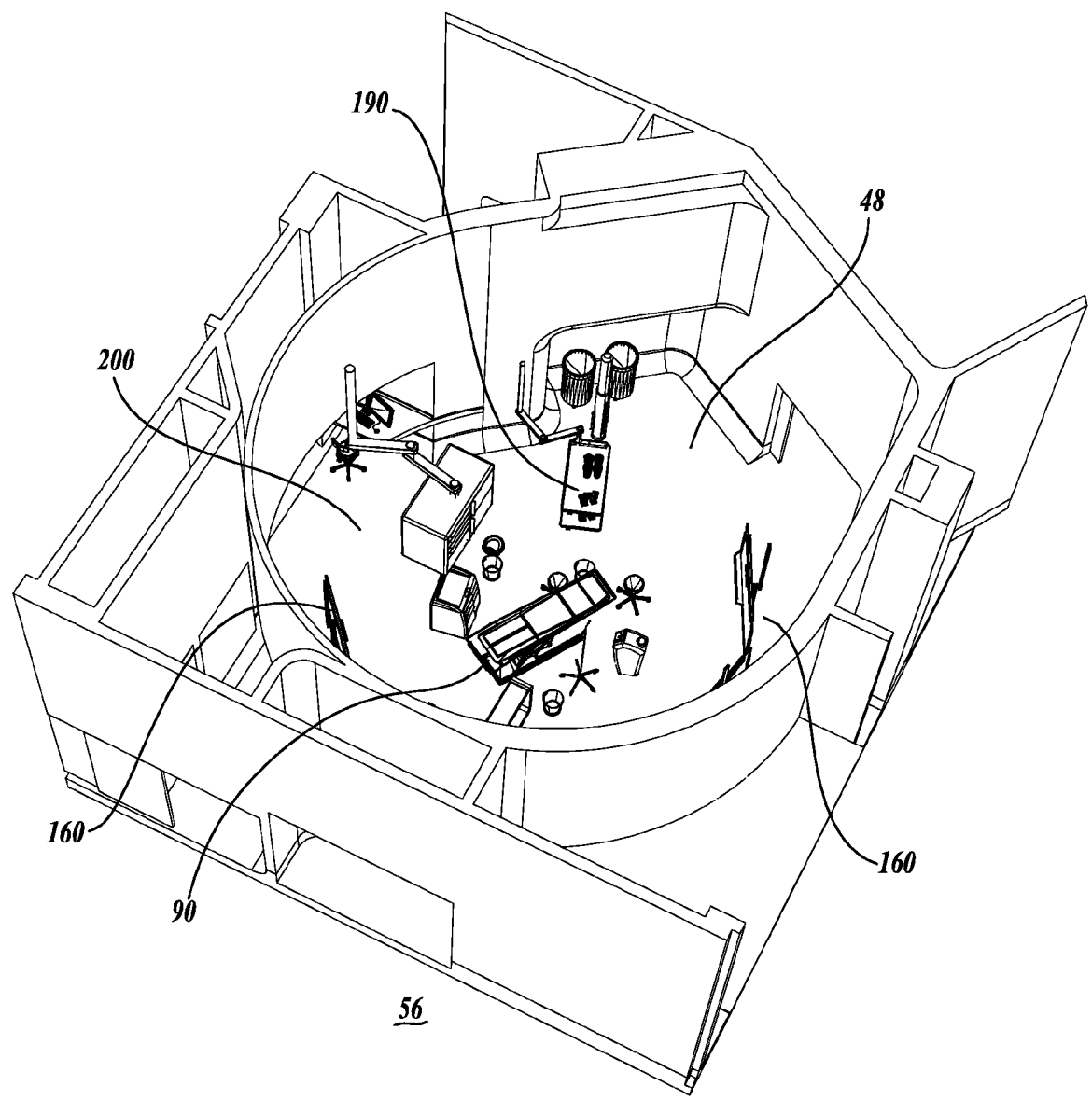
FIG. 11 is a perspective view of a high-acuity OR/intervention room.

To establish the surgery/intervention zone, medical gases, electrical and data outlets, vacuum lines, evacuation lines, and communication lines, are brought into the OR/intervention room through an interstitial space located in the floor for connection to the base portion of the surgical table 90. A connector hub assembly 107 for such medical gases, utilities, data, communications, vacuum, and evacuation, as shown in FIG. 10B, is located centrally in the surgery/intervention zone for automatic and secure connection to the base 244 of the surgical table 90 when the surgical table is positioned over the connector hub assembly. FIG. 10B shows various lines that enter into the OR/intervention room 46 through a sleeve 108 in the floor 142. The lines can include, for example, a vacuum line 110, a power line 111, a gas line 112, and a data line 113. Additional or alternative lines can be provided for other fluids and purposes, such as oxygen or nitrous oxide. Preferably, the sleeve and lines 110-113 are hermetically sealed at the floor 142.

Continuing to refer to FIG. 10B, the hub assembly 107 includes a connection collar 114 for securely supporting the ends of the lines 110-113. The connection collar 114 can be received in close registry within an indexing socket or cavity 115 at the bottom of the table base 244, so that the terminal ends of line 110-113 are disposed in registry with the lower ends of corresponding lines 110A, 111A, 112A and 113A, having associated connectors 110B, 111B, 112B, and 113B. The connectors 110B-113B may be powered or otherwise configured to automatically engage with the corresponding ends of lines 110-113 when the collar 114 is properly indexed with socket 115. The present invention also contemplates a digital monitoring system 116 for receiving lines 110A-113A, and for monitoring and controlling the gas, liquid or other fluid or data or electricity flowing through such lines.

Although the hub assembly 107 is illustrated as utilized in conjunction with the base 244 of the surgical table 90, alternatively or in addition, the same or similar hub arrangement may be utilized in conjunction with the anesthesia machine 92 when docked with the surgical table 90, as discussed below. Also, when the surgical table 90 and/or anesthesia machine 92 is disengaged from hub assembly 107, the adjacent ends of the lines 110-113 and 110A-113A are automatically closed to prevent gas/liquid/data flow or contamination.

Alternatively, the water-tight collar 114 may be flush with the floor surface when not in use to permit unobstructed cleaning of the floor between cases. The collar may be motorized to raise automatically from the floor surface for quick connection and disconnection to the utility portals in the surgical table.

To establish a surgical/intervention zone, the OR/intervention room 46 is free from the typical lights mounted on articulated arms suspended from the ceiling. Such arms are difficult to manipulate and create barriers between medical personnel, as well as block sightlines of the personnel. Moreover, such arms, as well as the lighting fixtures themselves, interfere with the laminar airflow over the surgical/intervention site, as discussed more fully below.

In the present situation, multiple lights 118 are positioned in recesses 120 formed in the ceiling. The lights may be of various types, including, for example, halogen or xeon lights. As shown in FIG. 10A, the lights 118 may include a bulb 122 mounted in a socket assembly 124. A high performance reflector 126, for instance a cold mirrored glass reflector, may be used to direct the light from the bulb 122. The lights include individual mounting systems 128 that enable the direction of the lights to be moved or manipulated, and focused as desired. For example, the light 118 can be tilted and swiveled about the mounting system to direct the light as desired. Actuation of the mounting systems may be by microchip-driven radio frequency controls or other types of controls positioned in the glove of surgical/intervention room personnel to enable the lights to be aimed and focused as desired as well as the intensity of the light to be varied. Rather than being mounted on a glove, the microchip controls can be mounted in other locations, such as on a wrist band, or head band of OR/intervention room personnel.

The light controls can also be tied to a radio frequency identification device or tag that can be embedded in or mounted on a clamp or other device located within the surgical/intervention zone that would remain static in the area during the procedure. Further, the lights can be pre-set by an automatic lighting system based on the procedure being performed. In this regard, the positioning of the lights can be programmed using a wall panel or remote control unit, or controlled from a central computer system. Additionally, or alternatively, the lights can be voice actuated. Lights of the nature of the present invention are articles of commerce, but retrofitted with special high intensity bulbs capable of achieving optimum focal length from the surface of the OR/intervention room ceiling to the surgical/intervention site. As shown in FIG. 10, substantially the entire ceiling portion of the intervention zone is covered with openings 120 for placement of the lights for the present invention.

As mentioned previously, in current OR/intervention rooms, light fixtures, utility cord drops, and other items obstruct the laminar air flow from the ceiling of the OR/intervention room to the surgical/intervention site This situation is corrected by establishing the surgical/intervention zone in the OR/intervention room, including by eliminating typical boom-mounted light fixtures. As a consequence, air can be introduced into the OR/intervention room through openings 120 similar to those used for the lights, and the air can flow, unobstructed, in a laminar manner down to the surgical/intervention site and out through exit outlets 140 located about the OR/intervention room near the floor 142.

As shown in FIGS. 5 and 9, relatively deep wells 144 are formed in the interstitial space above the ceiling of the OR/intervention room where the ventilation air that is routed downwardly into the OR/intervention room through ceiling panel diffusers using openings 120. Use of the ventilation wells 144 ensures that a uniform flow of ventilation air is supplied to the entire volume of the OR/intervention rooms, so that no significant "dead air" space exists. Moreover, with the elimination of lighting fixtures, equipment, etc., from the intervention zone, air flow eddies are eliminated within the laminar air flow to the surgical/intervention site.

Other sources of "congestion" in the OR/intervention room are the various monitors used to display physiological data of the patient, anesthesia data, as well as for image guidance, for example, during laparoscopic surgery or other procedures that utilize endoscopic cameras. Moreover, these monitors and display screens block light from the typical lighting fixtures used in OR/intervention rooms, as well as block the flow of ventilation air. Such monitors currently typically are mounted on articulating booms suspended from the ceiling within the surgical intervention zone.

In accordance with the present invention, a plurality of large flat screen monitors 160 are arrayed outside of the surgical/intervention zone. In this regard, see also FIG. 14 which illustrates a high-acuity OR/intervention room 48. The monitors are suspended from arms 162 that suspend downwardly from a rail system extending around the perimeter of the OR/intervention room outwardly of the intervention zone. The monitors may be of various types, such as plasma screen monitors, LCD screen monitors, etc. The important point is that the monitors 160 are of a size and high resolution so that their content may be easily viewed by the personnel in the OR/intervention room. The monitors include screens 164 that are supported by a mounting structure 166 that enables the screens to be adjusted both vertically and horizontally. In addition, the mounting structure 166 can be designed to enable the screens 164 to be rotatable about a vertical axis, and also about a horizontal axis for better viewing by personnel. To this end, the mounting structure 166 may include upper and lower tracks 168 and 170 as well as vertical end tracks 172 for guiding horizontal and vertical movement of the screens 164. Alternatively, the mounting structure 166 may be designed to move vertically relative to arms 162. The position of the screens can be controlled by voice command. The content of the screens can also be controlled by voice command. Moreover, the instruments and other devices that are being monitored on the screens 164 may also be controlled by voice command. Such control systems are articles of commerce. Voice recognition software is commercially available for use with voice command systems. The large screen monitor may be pre-programmed and arrayed for specific procedures and individual surgeon/interventionist preferences.

To create the surgical/intervention zone, a perimeter ring or rail system 180 is formed in the ceiling of the OR/intervention room around a perimeter thereof. As shown in FIG. 10, arms extend downwardly from the rail system to support previously floor-mounted tables, equipment, and cabinets. For example, a vertical arm 184 is illustrated as extending downwardly from rail system 180 to support the distal end of a first horizontal articulating arm 186 which in turn is pivotally coupled to a second horizontal articulating arm 186. A telescoping vertical arm system 188 extends downwardly from the proximal end of horizontal arm 186. The corners of two vertically spaced apart upper and lower shelves 190 and 192 are coupled to telescoping arm 188 by collar assemblies 194. The collar assemblies allow the shelves 190 and 192 to pivot relative to telescoping arm assembly 188 and then lock in position once the position of the shelves is as desired. A telescoping arm assembly 188 enables the shelves 190 and 192 to be raised and lowered as desired. When the shelves 190 and 192 are not in use, they can be removed beyond the intervention zone by rotation of horizontal arms 184 and 186. The movement of such arms, as well as the operation of telescoping arms 188, can be controlled by various means, such as a remote control device. Also, the movement of such arms can also be controlled by voice command.

FIG. 10 also illustrates cabinet 200 which is mounted on a pair of horizontal articulating arms 202 and 204, which in turn are supported by a vertical arm 206 that extends downwardly from track system 180. The cabinet 200 may include shelves and drawers for storing various instruments, supplies, and other equipment. Cabinet 200 can be positioned by personnel at desired locations by remote control or by voice command, in the manner of the shelves 190 and 192. As with the shelves 190 and 192, the cabinet 200 can be moved out of the way, and outwardly of the surgical/intervention zone, when not in use.

Figure 14:
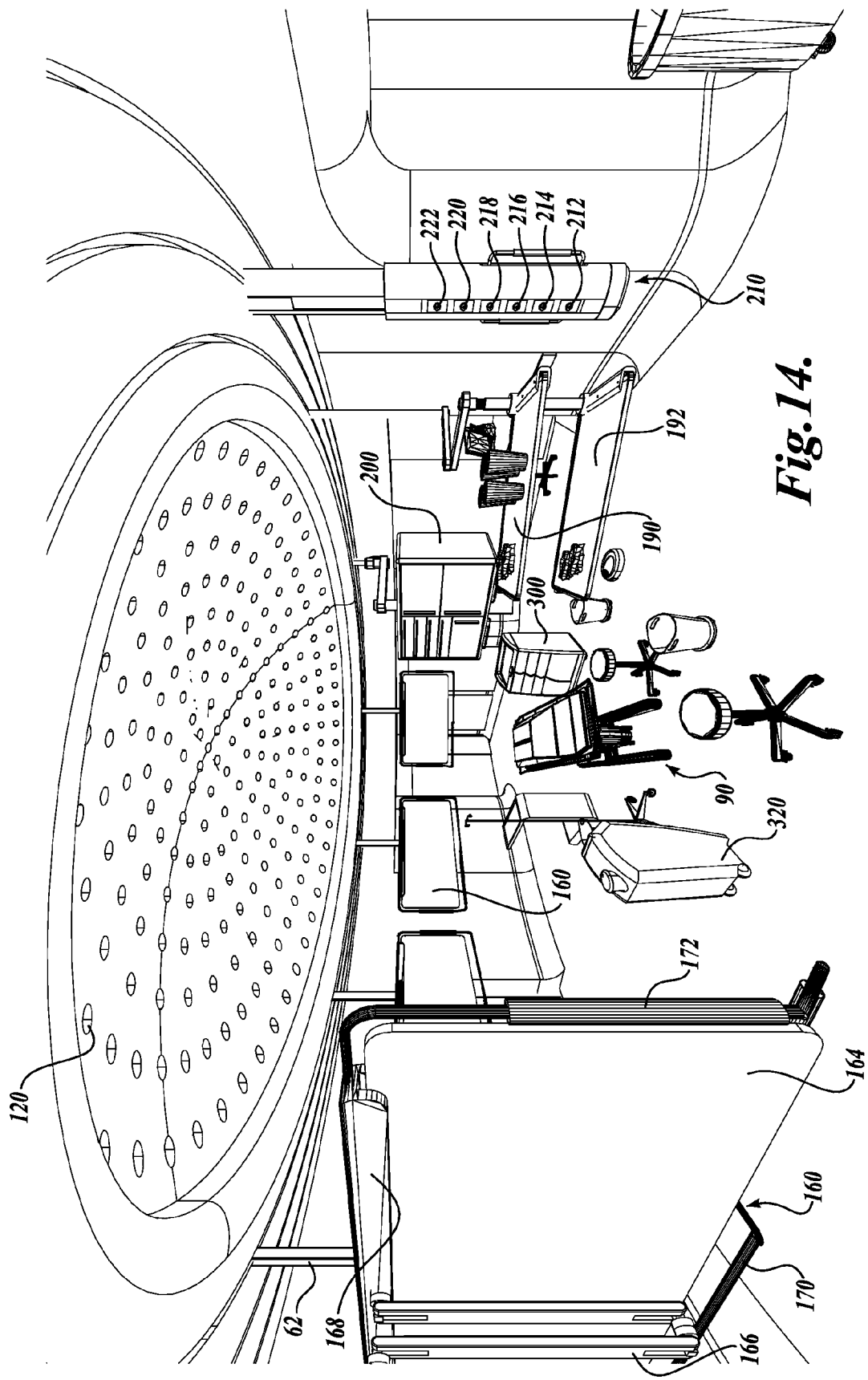
FIG. 14 is a further perspective view of a portion of a high-acuity OR/intervention room illustrating the intervention zone created by the present invention.

Referring to FIG. 14, utilities needed for cauteries, lasers, drills, and other accessories may be stationed remote from the surgical/intervention zone as a secondary utility distribution system from that provided in the floor 142. Such utilities can be provided in a vertical arrayed mounting system 210 which illustrates various medical gas, electrical, data and communications outlets 212-222. Such outlets will supplement corresponding outlets provided in the floor of the OR/intervention room beneath the table 90. It will be appreciated that the above described lighting system, monitors, table supports, cabinet supports, and auxiliary utilities allow elimination of virtually all ceiling and floor mounted obstructions in the surgical/intervention zone. Moreover, they also keep the floor free from obstructions whereby the floor can be cleaned by automated robots, described below.

Figure 15:
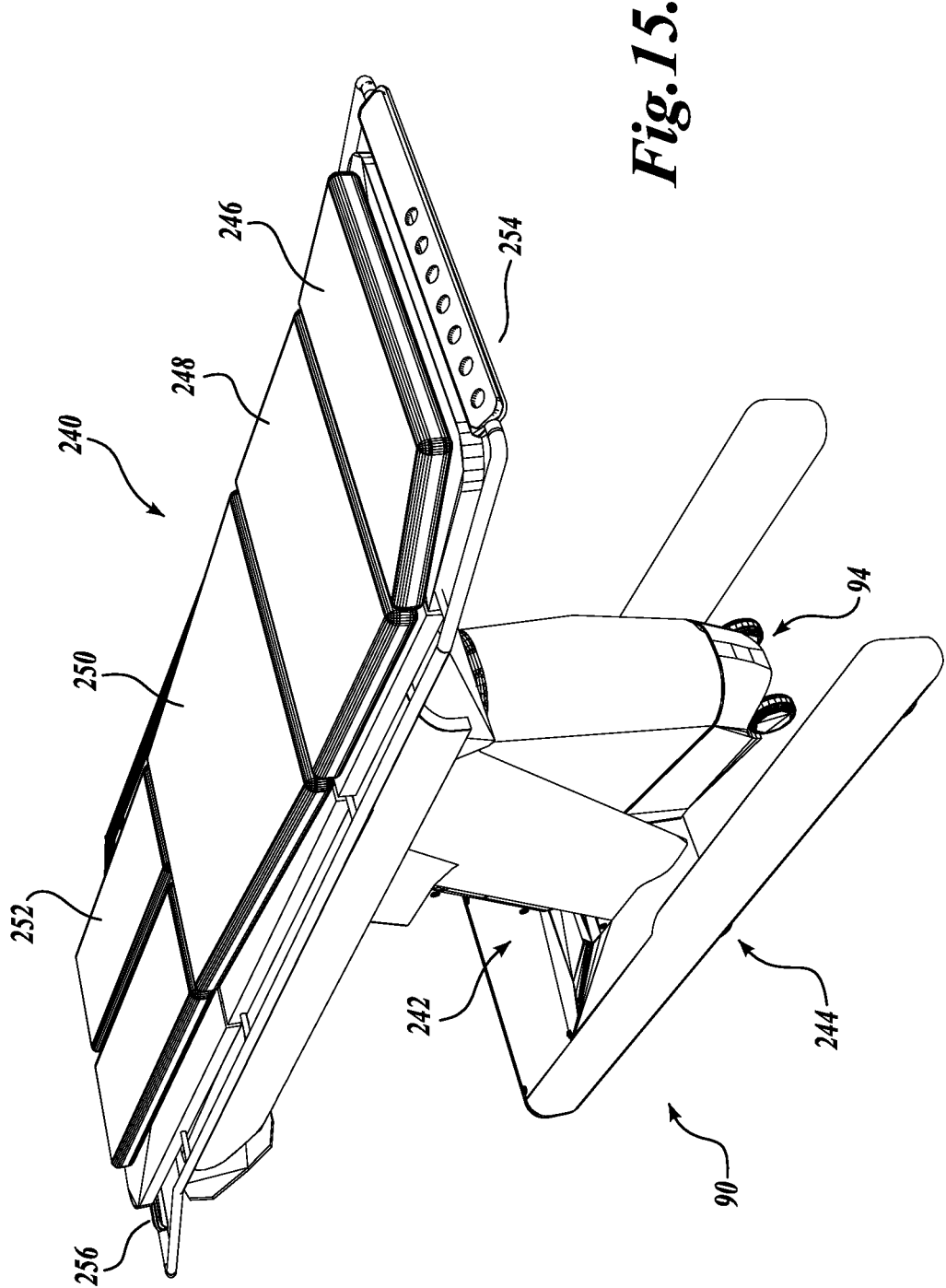
FIG. 15 is an isometric view of a surgical table in accordance with the present invention with an anesthesiology machine dock thereto.
Figure 16:
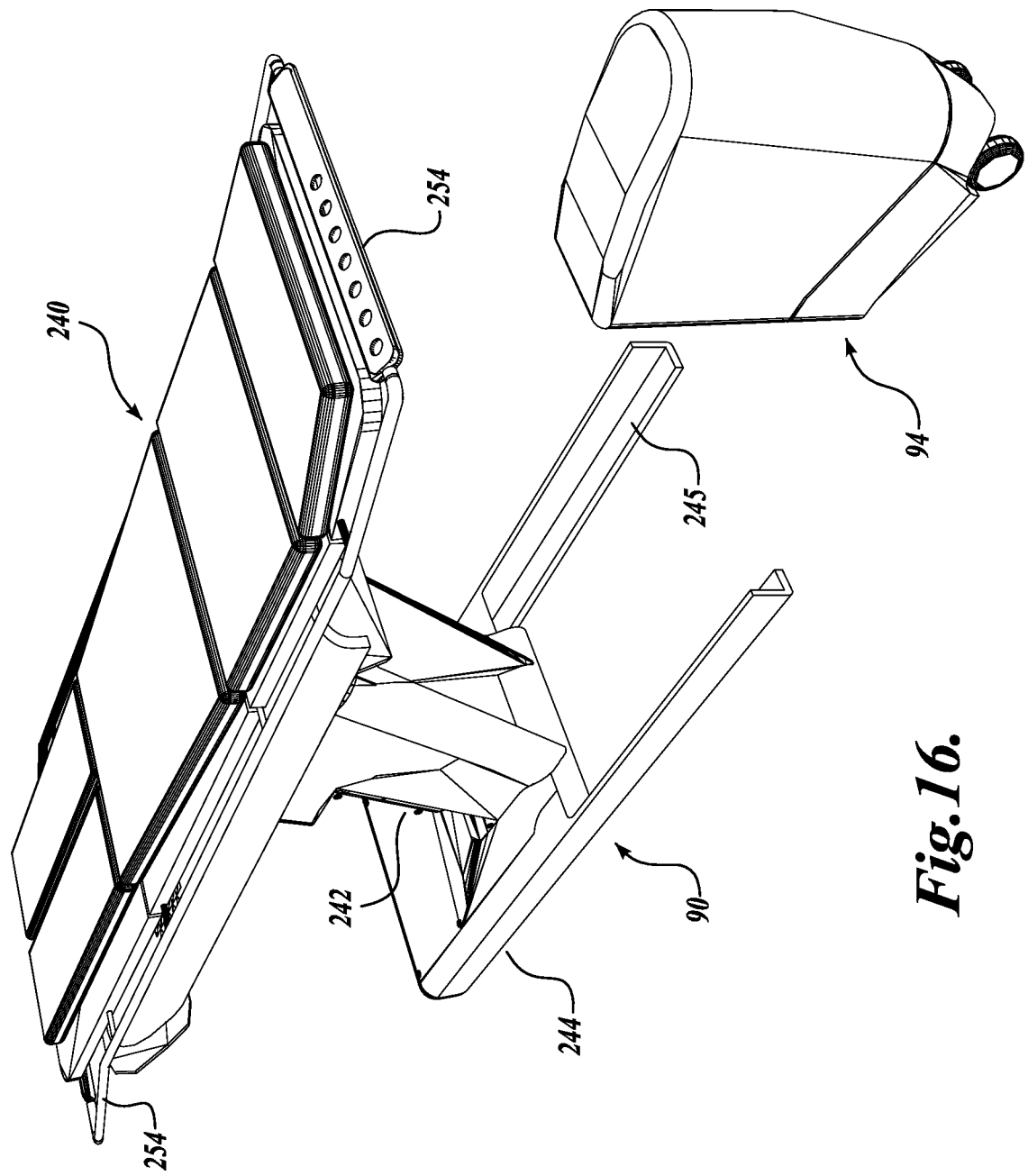
FIG. 16 is the view similar to FIG. 15 but with the anesthesia machine dedocked therefrom.

Next, describing the surgical table 90 in greater detail, referring specifically to FIGS. 10, 15, and 16, in basic form, the table includes a top portion 240, a pedestal portion 242, and a base portion 244. The top portion 240 is constructed in various sections, including a head section 246, a shoulder section 248, a torso section 250, and a lower extremity section 252. Each section may be pivotable or elevatable relative to the adjacent section.

The retractable arm structures 254 and 256 are positioned at the head and foot of the tabletop 240, on which are mounted outlets for all medical gases, vacuum source, evacuation source, electrical supply, data and communications that are brought into the OR/intervention room through the floor 142, as described above. The arm structures 254 and 256 include connections that are made at an ergonomically correct height and then are rotatable downward to a position below the surgery intervention table surface so as to move out of the way and not be accidentally bumped. Also by locating the arm structures at the head and foot of the table 90, the outlets are maintained clear of a sterile surgical drape which may be clamped on the sides of the patient. Further, an arm structure is accessible to the anesthesiologist located at the head of the patient.

The medical gases, vacuum, utilities, data lines, tubes, and cords are routed to the arms 254 and 256 through pedestal 242 from the base 244. As mentioned previously, the base has a connector assembly that connects with the connector hub located in the OR/intervention room floor 142. In this manner, ceiling drops, columns, and articulating booms and cords to carry medical gases, vacuum, evacuation, electrical, and data to the location of the immediate patient area are eliminated.

As previously discussed, the same table 90 is used to support the patient from the intubation room 52, the OR/intervention room 46 and the extubation room 54. As such, the surgical table 90 is provided with wheels in the base 244 to enable the table to be easily moved from place to place. As also mentioned above, an anesthesia machine 94 is configured to be dockable and dedockable to the table base 244. The anesthesia machine 94 has quick disconnect fittings to connectors located on the table base 244 or pedestal 242, which, in turn, are connected to the utility hub in the floor 142. Anesthesia outlets may also be incorporated into the table arm structure 254 and 256. By this construction, the anesthesia machine 94 is independently mobile relative to the table for cleaning and servicing. Moreover, the anesthesia machine may be controlled by an anesthesiologist or technician in a remote control room. As such, physical intervention and manipulation of the anesthesia machine in the OR/intervention room is not required. Of course, a nurse anesthesiologist may be present in the OR/intervention room to administer to the patient. However, the anesthesiologist can move from OR/intervention room to OR/intervention room or be located in a remote control room to monitor a number of patients at one time, thereby increasing efficiency of the anesthesiologist and safety of the patient.

Figure 15A:
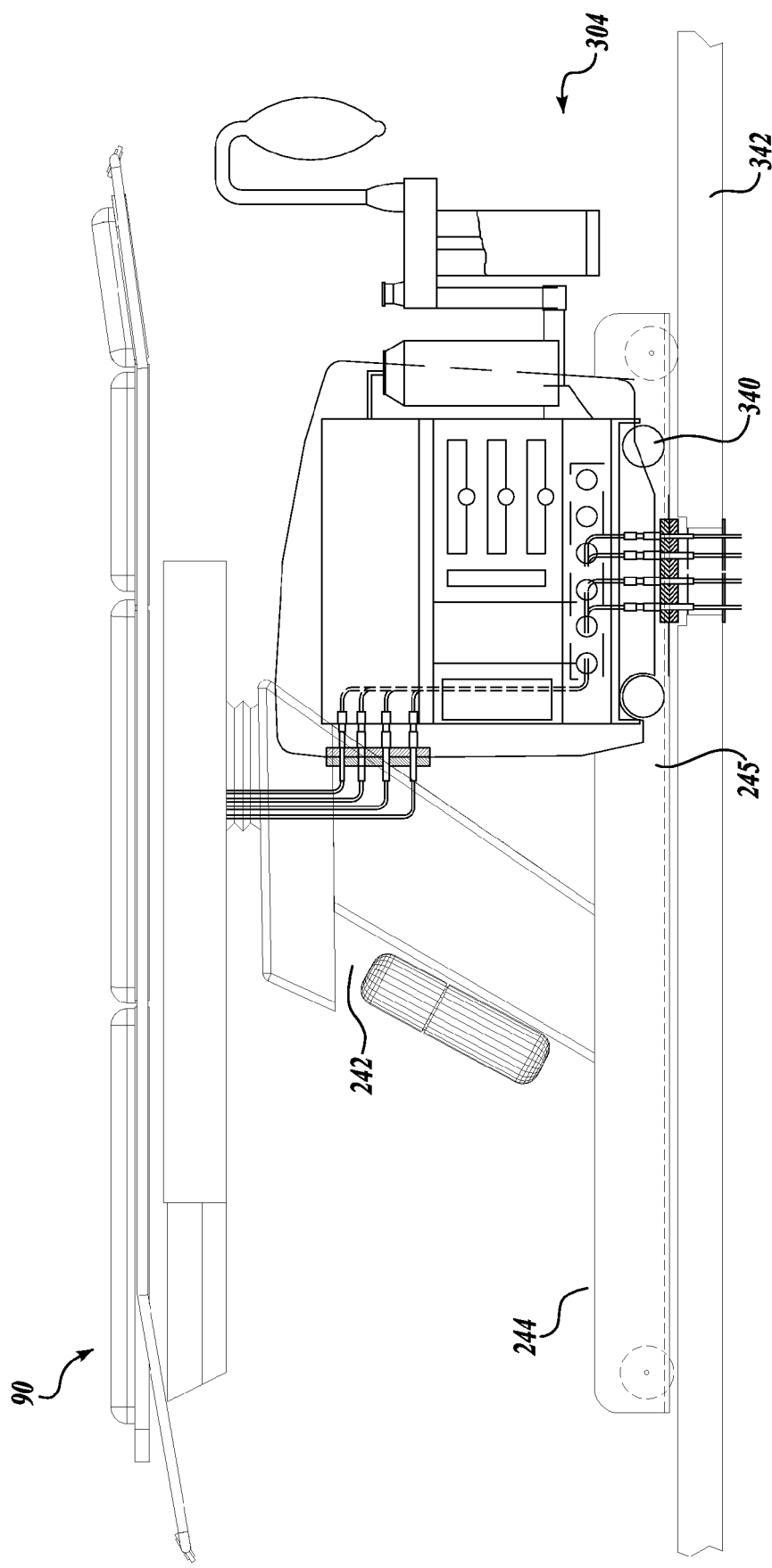
FIG. 15A is a side elevational view of a surgical table with an anesthesia machine docked therewith, the anesthesia machine is connected to a floor hub to supply medical gases, a vacuum source, electricity, data and other utilities to the anesthesia machine.
Figure 15B:
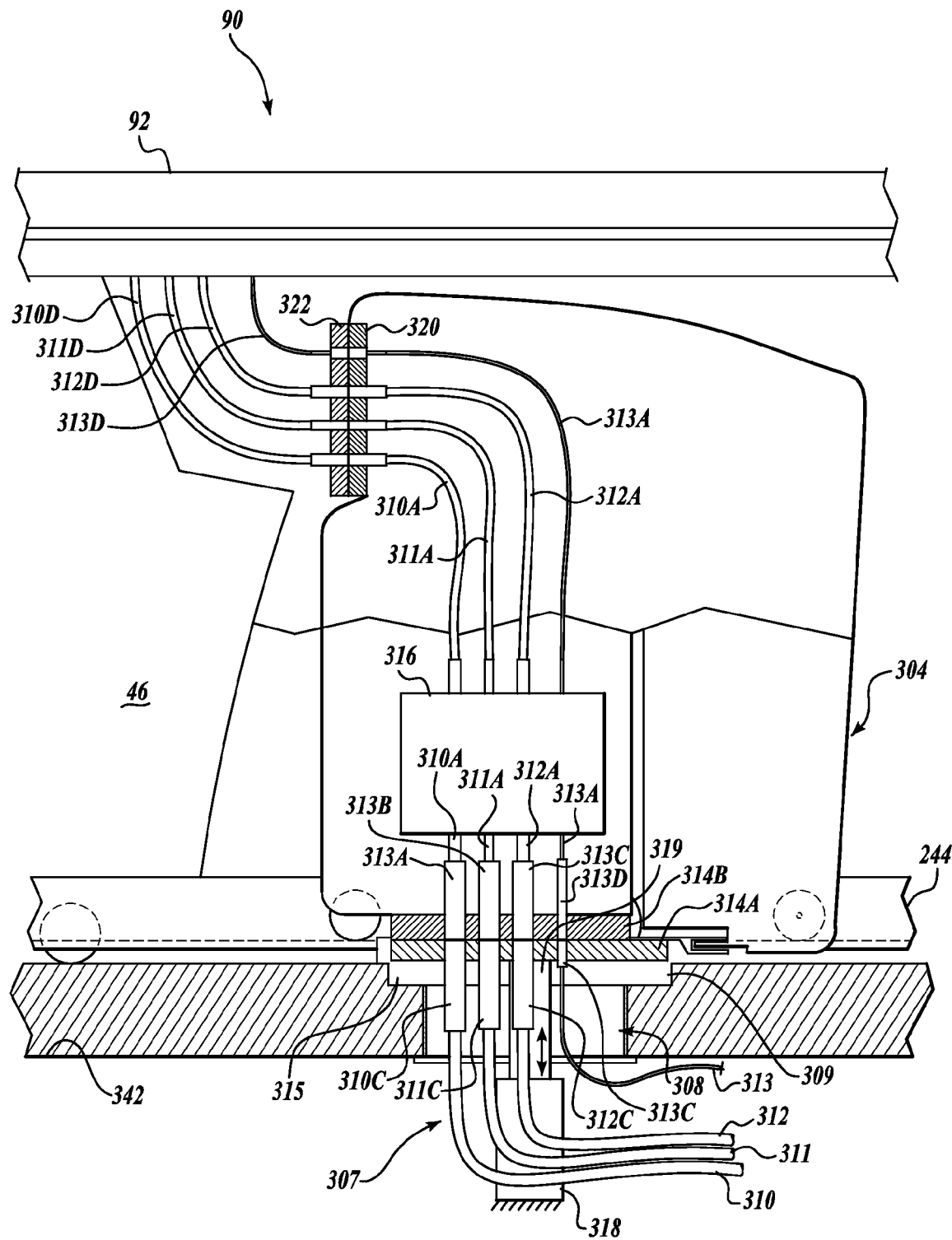
FIG. 15B is an enlarged, fragmentary view of FIG. 15A, showing the connection hub in larger scale.

FIGS. 15A and 15B illustrate an anesthesia machine 304, docked with surgical table 90, but with the anesthesia machine coupled to a hub assembly 307 in a manner similar to hub 107 coupled to the surgical table 90 shown in FIG. 10B. In FIGS. 15A and 15B the components similar to those shown in FIG. 10B are given corresponding part numbers but as a "300" series.

As in FIG. 10B, in FIGS. 15A and 15B medical gases, vacuum lines, evacuation lines, electrical and data outlets and communication lines are interfaced with the OR/intervention room through an interstitial space located in floor 342 for connection to the base portion of anesthesia machine 304. As in FIG. 10B, a connector hub assembly 307 is utilized for such medical gases, utilities, data, communications, vacuum and evacuation. The connection hub assembly 307 includes a lower connection collar 314A that is nominally disposed within a recess 309 formed in the floor 342. The collar 314A may be raised upwardly into engagement with a corresponding collar 314B, positioned at the base portion of the anesthesia machine. The upward extension or downward retraction of the lower collar 314A is via linear actuator 318 connected to the collar 314A via push-pull rod 319.

As shown in FIGS. 15A and 15B, the terminal ends of vacuum line 310, power line 311, gas line 312, and data line 313, are attached to connection collar 314A. Connectors 310C, 311C, 312C, and 313C are provided for the lines 310-313, which connectors are held securely by the connection collar.

The lines 310, 311, 312, and 313 are connectable to the lower ends of corresponding lines 310A, 311A, 312A, and 313A, which extend downwardly from the anesthesia machine to terminate at connectors 310B, 311B, 312B, and 313B, securely held by upper collar 314B. As in FIG. 10B, a control and monitoring system 316 is interposed in lines 310A-313A for monitoring and controlling the gas, liquid or other fluids, or evacuation or data or electricity transmitted through such lines. Also, when lower connection collar 314A is in refracted position within recess 309, connectors 310C, 311C, 312C, and 313C automatically close off corresponding lines 310, 311, 312, and 313.

When the anesthesia machine 304 is docked with surgical table 90, lines 310A, 311A, 312A, and 313A automatically connect to corresponding lines 310D, 311D, 312D, and 313D of the surgical table 90. To this end, a second set of connection collars 320 and 322 are provided between the anesthesia machine and the surgical table. The collars 320 and 322 automatically mate with each other upon the docking of the anesthesia machine with the surgical table, thereby to permit flow between lines 310A-313A to corresponding lines 310D-313D. As in connection collar 314A, one or both of the connection collars 320 and 322 can be designed to extend forwardly or retract rearwardly to lock with the corresponding connection collar. When the anesthesia machine and surgical table are disengaged from each other, the adjacent ends of lines 310A-313A and 310D-313D are automatically closed to prevent gas, liquid, data, vacuum, electrical flow or contamination.

As an alternative to the foregoing, when the anesthesia machine 304 is docked with surgical table 90, a hub assembly similar to hub 307 can be used to connect utilities, gases, data, to the surgical table rather than to the anesthesia machine. In this option, when the anesthesia machine is docked with the surgical table, a connection system is utilized at the lower portion of the anesthesia machine to connect to the surgical table, in a manner similar to connection collars 320 and 322. In this situation, the anesthesia machine controls the flow of gases and other utilities to and from the surgical table in a manner similar to that contemplated in the embodiment of the present disclosure shown in FIGS. 15A and 15B. This may be a less desirable option than having the hub assembly 307 connectible to the anesthesia machine, since it requires that the surgical table also be configured to connect to the hub assembly, thereby duplicating the connection capabilities of the anesthesia machine.

In FIG. 15, the anesthesia machine 94 is shown as supported on the floor 342 by wheels. As an alternative, when the anesthesia machine 304 is docked with surgical table 90, the anesthesia machine could be carried by and supported by the surgical table. To this end, wheel channels or supports (not shown) could extend along the inside portions of rails 245 of base 244 of the surgical table to receive wheels 340 of the anesthesia machine 304.

Another source of expense and inefficiency in a typical hospital or medical clinic setting is that patients must be transported from OR/intervention rooms to remote locations where imaging equipment is located. Alternatively, the costly imaging equipment may be dedicated to a single OR/intervention room. The transport of the patient to a remote imaging room can increase the incident of medical errors and compromise patient safety.

In accordance with the present invention, scanning equipment, for example, scanner 270, shown in FIGS. 8 and 10 may be brought into an OR/intervention room, as needed, by an overhead monorail system 272, as shown in FIGS. 8 and 9. The monorail system allows the scanner 270 to be moved among a number of OR/intervention rooms for real time use during an intervention procedure. When not needed in an OR/intervention room, the scanner can be used for routinely scheduled diagnostic studies in imaging suites 50, see FIG. 3. This enables the scanner to be used more efficiently than in existing hospitals and medical facilities.

Various types of scanners can be employed in the mobile manner of the present invention, including CT scanners, MRI machines, fluoroscopy C-arm, ultrasound, and other types of scanners. As shown in FIG. 10, the scanner 270 is connected to the lower end of a vertical arm 274, with the upper end of the arm connected to a powered carriage 276 which moves along the monorail system 272. All required electrical and data services are provided by retractable cables. In the case of moveable MRI scanners, a telescoping duct system extends or retracts to exhaust cryogen gases in the event of an unexpected "quench" of the cryogen system. Appropriate retractable openings 278 can be formed in the walls of the OR/intervention rooms to allow passage of the vertical arm 274. The imaging equipment can be controlled and operated by a logistics core, for example, located at the center of a number of OR/intervention rooms. This provides for efficient usage of imaging equipment personnel.

Alternatively, the scanning device such as a CT or MRI scanner may be fixed in an imaging room positioned between two OR/intervention rooms. In this alternative, the patient is automatically transported from the surgical/intervention zone to the centrally located scanner on a commercially available surgical/intervention table.

Figure 12:
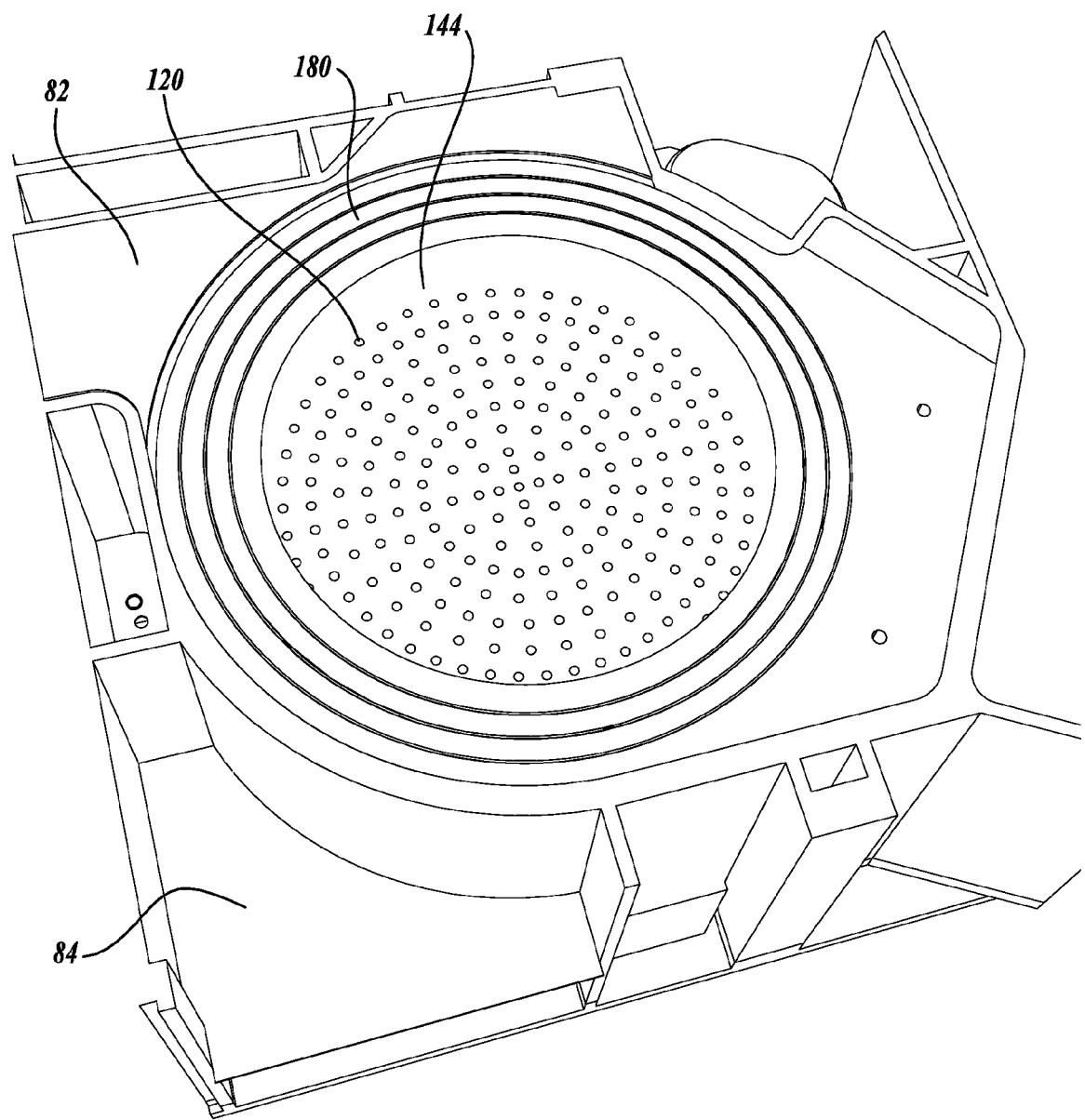
FIG. 12 is a perspective view of the area above the OR/intervention room of FIG. 11.
Figure 13:
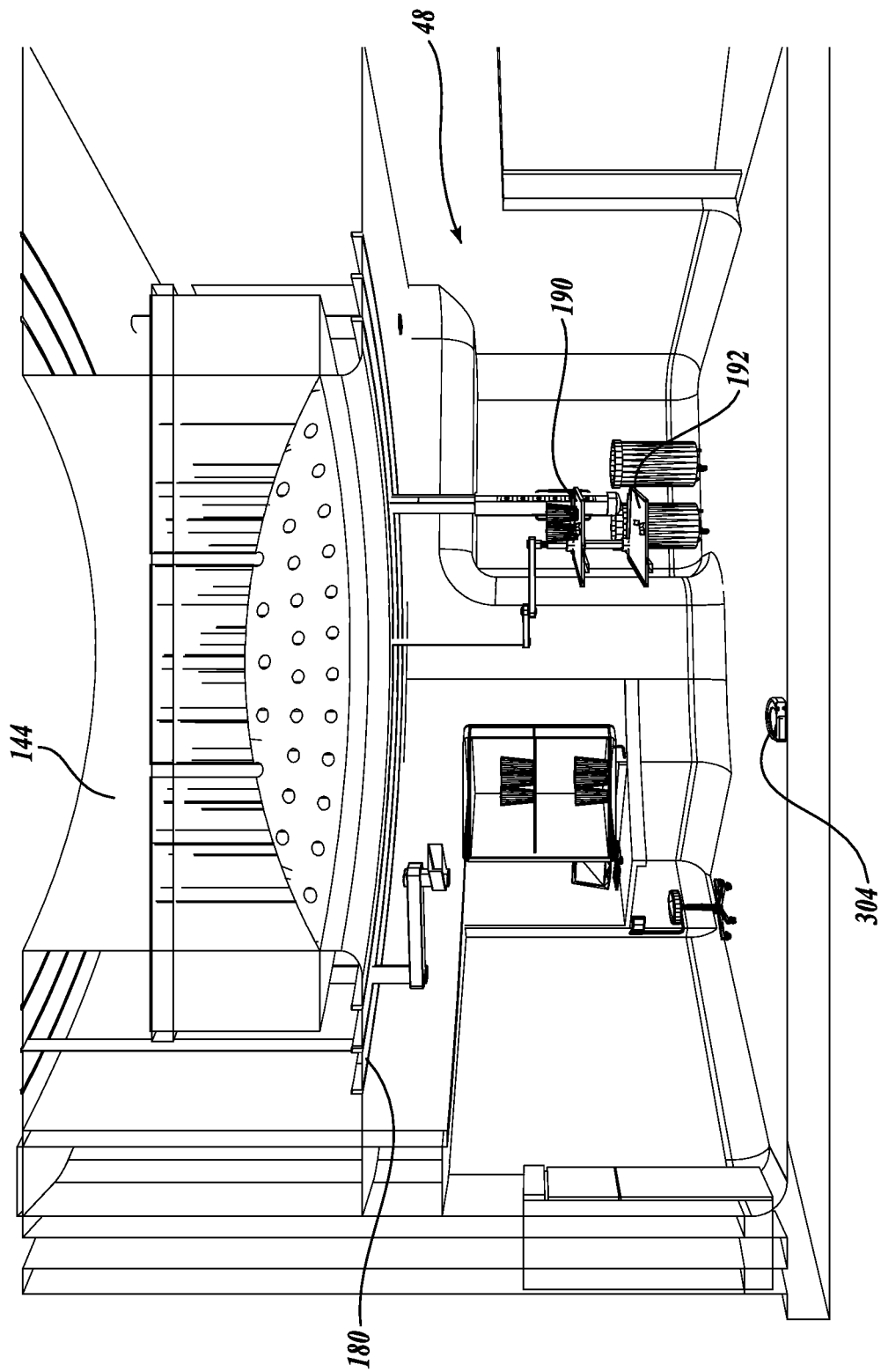
FIG. 13 is a perspective view of a portion of the OR/intervention room of FIG. 8 shown partly in cross-section.

FIGS. 8-10 illustrate OR/intervention room 46, which is specifically designed for relatively high volume usage, meaning for procedures of about two hours or less. To make maximum usage of the OR/intervention room 46 adjacent intubation and extubation rooms 52 and 54 are utilized, as described above. FIGS. 12-14 illustrate the high-acuity OR/intervention room 48 which is used for longer and more extensive procedures than in OR/intervention room 46. Such procedures may include, for example, orthopedic, general, craniofacial, cardiovascular interventions, neurological interventions and organ transplants. As such, intubation rooms and extubation rooms are typically not utilized with the high-acuity OR/intervention room 48. However, in other respects, the OR/intervention room 48 is constructed and laid out similarly to the OR/intervention room 46 described above. Thus, like components and structures used in OR/intervention room 48 are given the same part numbers as the corresponding structure/components used in OR/intervention room 46. As in OR/intervention rooms 46, the high-acuity OR/intervention rooms 48 also utilize mobile imaging equipment 270. Further, as in the high volume OR/intervention rooms, a surgical/intervention zone is established in the high-acuity OR/intervention rooms 48. In addition, as in the high volume OR/intervention room 46, the high-acuity OR/intervention room 48 includes a utilities hub in the floor of the room for connection to the base of the surgical table 90.

An area of hospital/clinical practice usage that has not kept pace with diagnostic and treatment technologies is materials logistics, supplying the instruments, equipment and other items needed in the OR/intervention room. These are typically delivered to the OR/intervention room manually and also removed from the OR/intervention room manually after usage.

Figure 17:
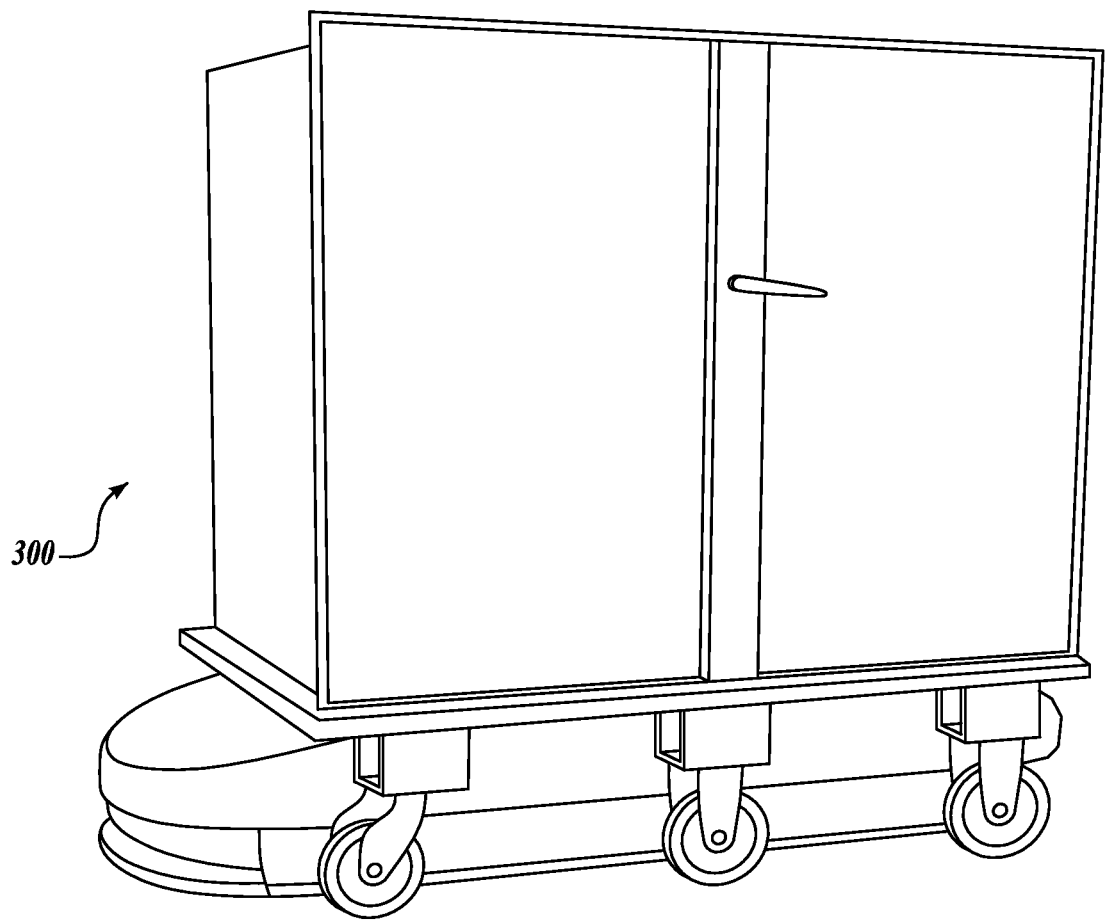
FIG. 17 is a perspective view of a typical robot used in conjunction with the present invention.

The present invention incorporates the use of robots to deliver case packs, supplies, instruments, etc., to the OR/intervention room and remove used linens, supplies, instruments from the OR/intervention room in an efficient and quick manner. Case packs and supply cabinets can be configured as part of a robot itself, for example, robot 300, shown in FIG. 17. Also, the instrument 302 shown in FIG. 14 may be incorporated into a robot. Such robots enter the room vertically by automatic cart lifts incorporated into the OR/intervention room, for example, along the perimeter thereof. The robots are delivered to the OR/intervention room from a logistics core, located at the center of a plurality of OR/intervention rooms. The deployment of the robots and their return to the logistics core can be completely or partially automated or controlled from the logistics core. The robots return soiled linens, instruments, equipment and waste to a decontamination area of Central Sterile Supply.

Robots of the foregoing nature are articles of commerce. Such robots are available, for example, from PYXIS Corporation. Such robots may operate without fixed tracks or guidewires. Another robot is marketed under the designation Transcar Automated Guided Vehicles from Swisslog HCS. Such robots are able to efficiently travel from location to location, avoiding stationary moving objects. Some may need elevators or lifts. Such robots announce their arrival at a destination, signaling closed doors to open and maintaining communications with a central computer system.

Instruments and re-usable supplies are frequently not available when needed in an OR/intervention room, often due to breakdowns in the logistics system. This may result in costly as well as dangerous or compromising delays during a procedure. As a consequence, greater inventories are often prescribed than actually needed, to compensate for such delays. The present invention contemplates tracking instruments and re-usable equipment with a radio frequency system, which is not affected by the sterilization process. Radio frequency tags may be mounted on, or incorporated into, such instruments and re-usable equipment. The location of such equipment can then be monitored or readily ascertained. As a consequence, instrument and re-usable equipment loss, as well as inventories, may be reduced, thereby resulting in lower operational costs, fewer or shorter delays, as well as reduced medical errors. Radio frequency tags are articles of commerce, as well as equipment from monitoring or reading such tags.

In another aspect of the present invention, OR/intervention rooms, as well as intubation and extubation rooms, are automatically cleaned between uses. Currently, OR/intervention rooms are manually cleaned requiring a significant length of time. As such, if existing clean durations can be reduced significantly, the number of surgical interventions performed in an OR/intervention room per day can be increased. To this end, the present invention incorporates the use of several cleaning robots 304 that are housed in the OR/intervention room or in the intubation/extubation rooms, see FIGS. 10 and 13. Such cleaning robots are capable of dispensing a biocidal cleaning solution onto the floor and then scrubbing and vacuuming the floor thoroughly. Such robots have a biocidal cleaning solution storage compartment, scrub brushes, a vacuum system, and a waste bin for collecting the used cleaning solution and other debris or items removed from the OR/intervention room floor. Waste cleaning solution and debris are automatically purged from the cleaning robots in their docked position. Cleaning robots somewhat similar to robots 304 are available from iRobot Corporation.

After cleaning by the cleaning robots, a biocide aerosol is dispensed into the OR/intervention room through ports in the ceiling. The aerosol decontaminates all surfaces of the OR/intervention room. The aerosol is exhausted from the OR/intervention room through the exhaust ports 140 located near the floor. The biocide aerosol is non-hazardous to humans, though typically staff will not be in the room during the cleaning process. Applicants estimate that the time for cleaning an OR/intervention room using the foregoing equipment and process to be reduced to about two minutes. This dramatically shortens cleaning time over current manual procedures.

A further aspect of the present invention to improve the quality and efficiency of hospital/clinical procedures is to utilize an automated hand/arm scrubbing system. Currently, manual scrubbing by the intervention team takes at least eight minutes. The present invention contemplates utilizing an automatic scrubber system, not shown, utilizing power brushes to gross clean the hands and arms of the surgical/intervention team members. The system could include efficient powered brushes to reach all areas of the users hands, fingers, and arms, as well as a biocide cleaning solution and sterile water for rinsing. The system also contemplates a self-cleaning system for the brushes after usage. After gross cleaning by the brushes, final cleaning occurs by the application of a biocidal solution, for instance, by spraying such solution onto the hands and arms of the user. Using the foregoing equipment and procedure, it is estimated that the time required for scrubbing can be reduced from eight minutes to approximately two minutes with greater effectiveness.

Alternatively, the hand wash system may not utilize brushes, but instead numerous rotating nozzles that automatically spray water and anti-bacterial solution on the hands and under the fingernails. Thereafter, the hands are rinsed with non-irritating, high-pressure water spray, and then dried with a built-in air dryer. Alternatively, paper towels can be used for drying. Such hand washers are articles of commerce, for example, available from Meritec, Inc., of Centennial, Colo.

Referring to FIG. 1, the method of the present invention is schematically illustrated. In accordance with the method, a patient is received at a medical/clinical facility at the concierge area 38 by personnel having information about the patient, the intervention to take place, and the schedule of the intervention. The patient is taken to a universal patient room 40. Here the patient can be admitted, and pre-preparation tasks performed. Also in the patient room, family members may be present. From the patient room 40, the patient is taken to the induction room 52 for induction tasks performed, including, for example, attachment of monitoring and fluid lines to the patient, performing anesthesiology on the patient, and carrying out final pre-intervention preparation of the patient. In the next step the patient is transported to the OR/intervention room 46, where the intervention is performed. As noted above, such interventions typically are of relatively short duration, typically two hours or less. After the intervention, the patient is transported to an adjacent extubation room 54 for extubation of the patient, including awakening the patient and possibly removing monitoring and fluid lines from the patient. Next, the patient is returned to the patient room for recovery. The patient room, as noted above, is adaptable to the acuity level required for the patient, from high level intensive care to traditional low level recovery and rest. Subsequently the patient is discharged directly from the patient room.

FIG. 2 is a schematic flow diagram similar to FIG. 1, but for high acuity interventions, wherein the intubation room 52 and extubation room 54 are not utilized. Rather, the patient is taken directly from the patient room 40 to the high acuity OR/intervention room 48 for performance of the intervention procedure. Thereafter the patient is taken directly from the OR/intervention room back to the patient room 40 for recovery.

Figure 18:
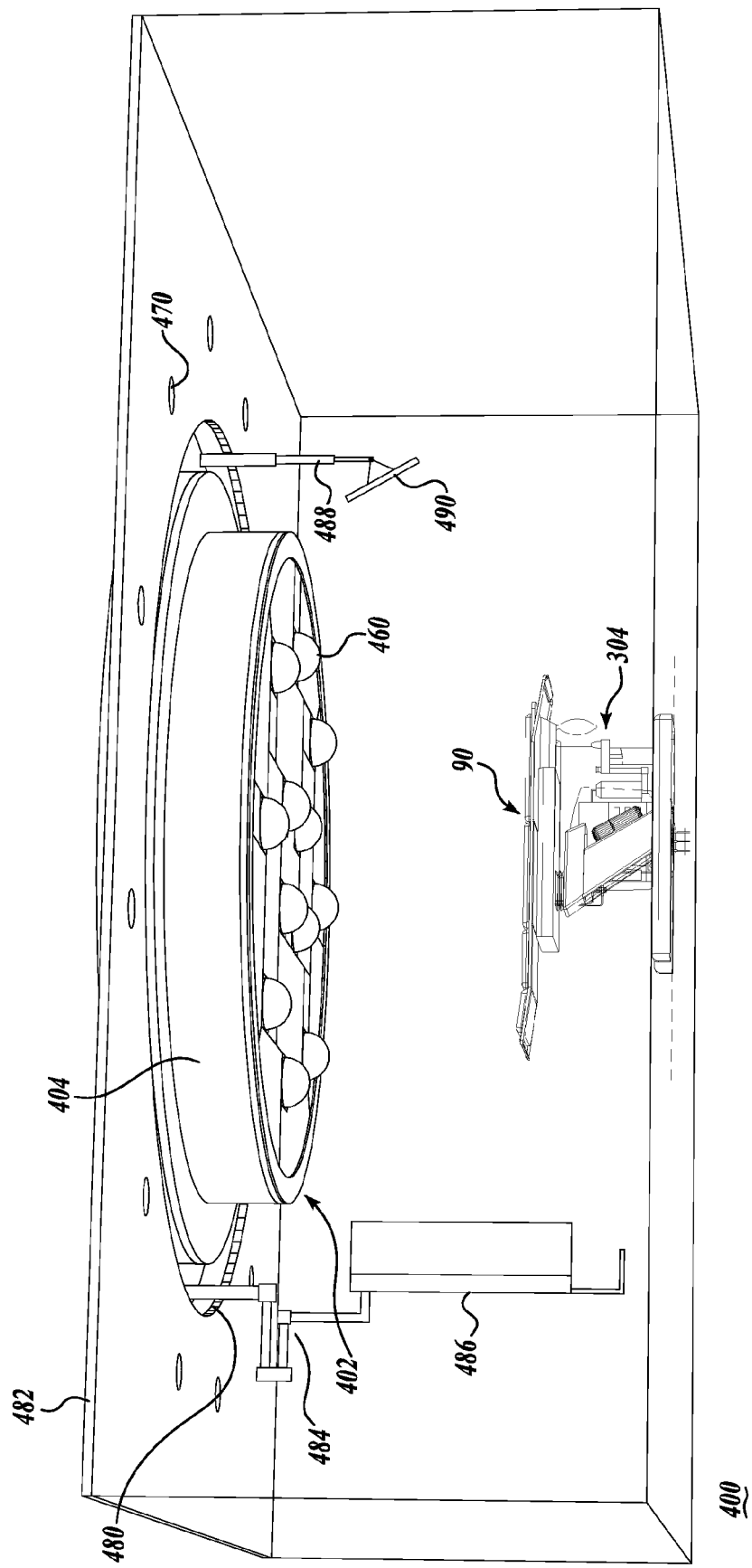
FIG. 18 is a perspective view of a portion of an OR/intervention room, looking upward toward a drop-down ceiling portion that defines the surgery/intervention zone.
Figure 19:
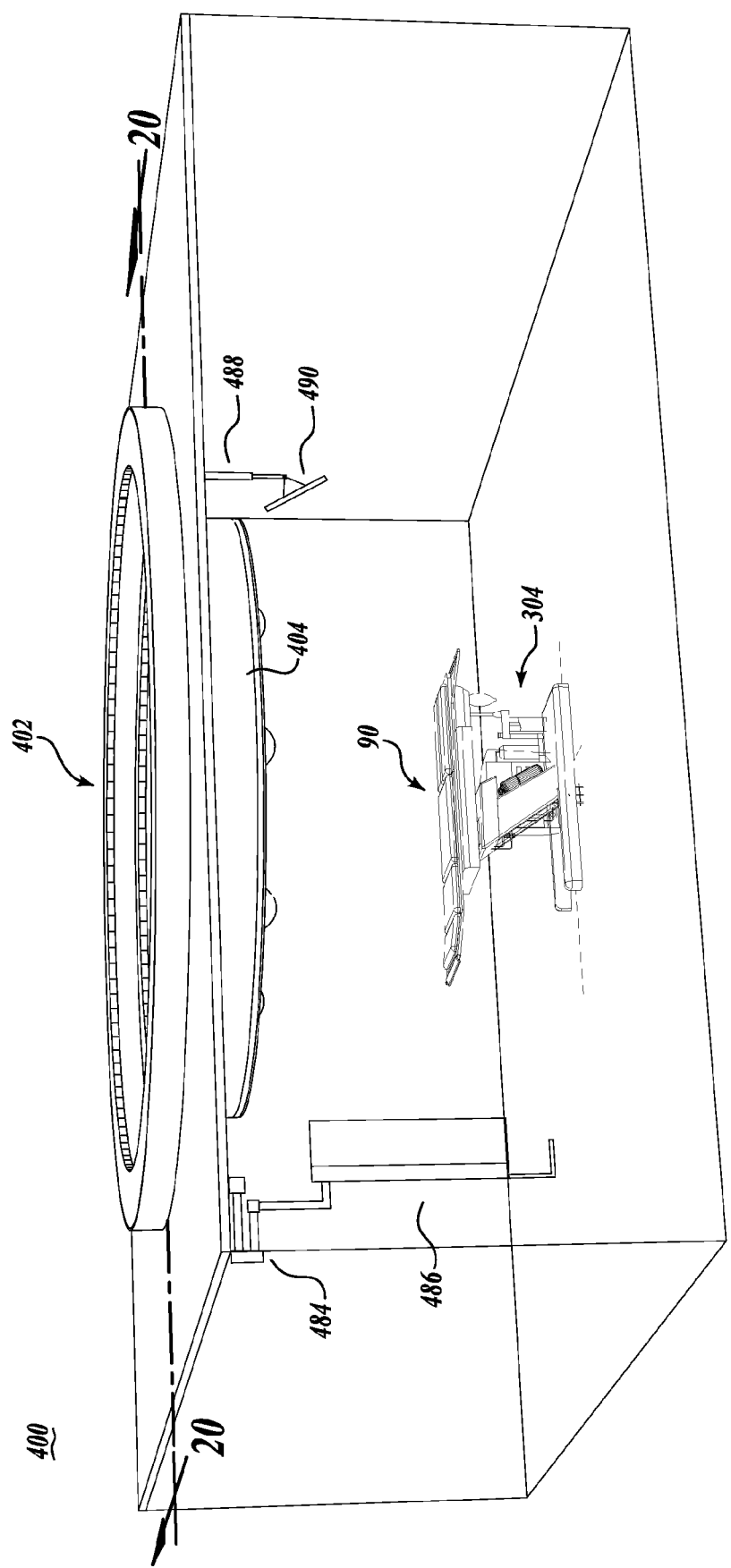
FIG. 19 is a view similar to FIG. 18, but taken in a downward direction.
Figure 20:
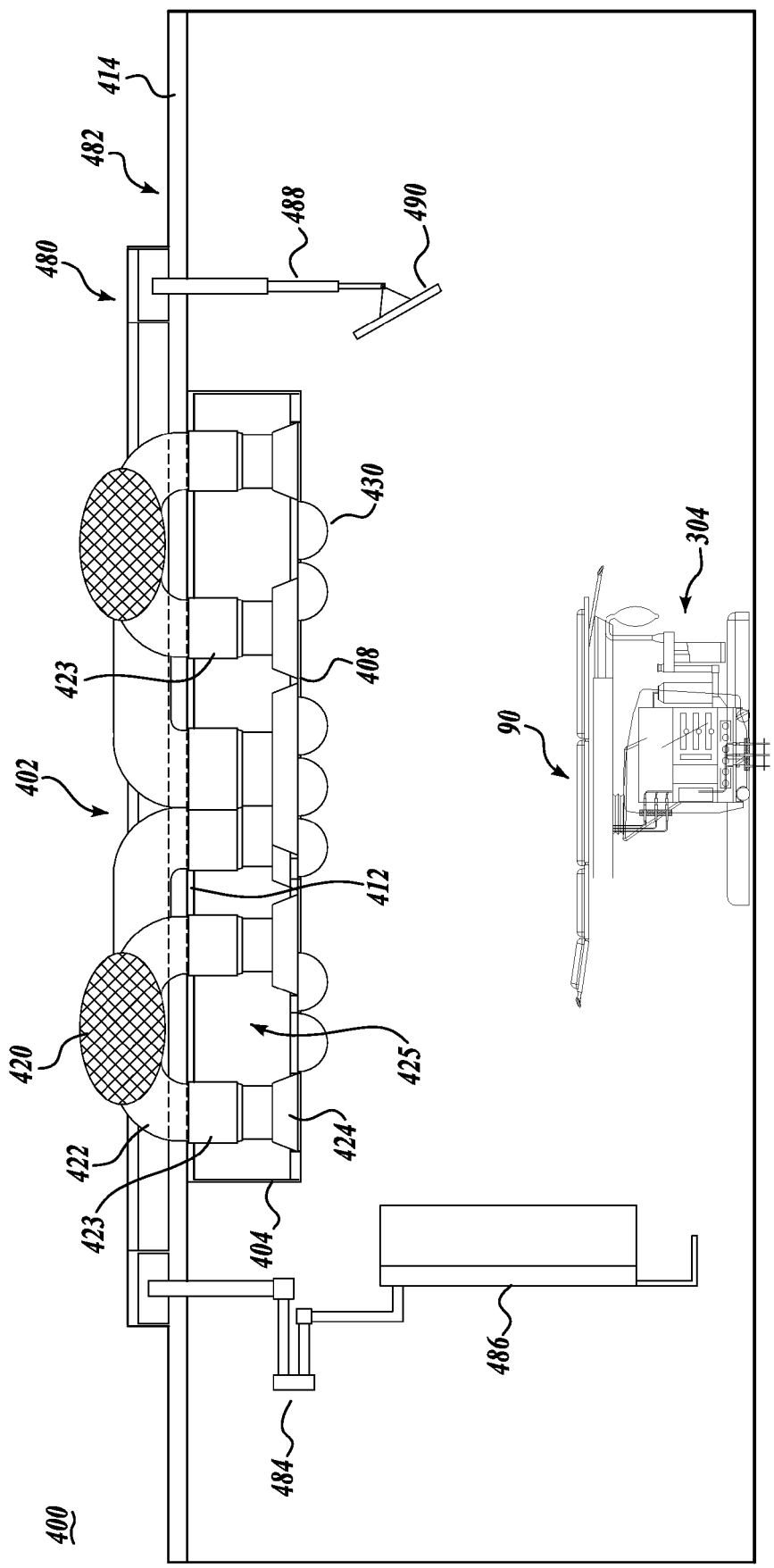
FIG. 20 is a cross-sectional view of the drop-down ceiling portion of FIG. 19.

Next, referring to FIGS. 18, 19, and 20, a further disclosure of an OR/intervention room 400 constructed and operationally very similar to the other OR/intervention rooms of the present application. The OR/intervention room 400 includes a drop-down ceiling structure 402 which is shown as being circular in shape to define the surgery/intervention zone around the patient that is free from articulating arms, from monitors, lighting, equipment, etc., and also free from hose drops and utility columns from the ceiling or other electrical, data, medical gas, vacuum or evacuation lines, tubes, or cords. The surgical/intervention zone may be of a selected size defined by the size of the drop-down ceiling structure 402 which may be from, for example, 10-20 feet in diameter. As previously discussed, this establishes an unobstructed sterile zone for the surgery/intervention team to freely and efficiently function within.

As shown in FIGS. 18-20, the drop-down ceiling structure 402 extends downwardly from the ceiling height of the rest of the OR/intervention room 400, with the ceiling height of structure 402 being, in one disclosure of the present application, approximately 7.5 feet above the floor. Of course, this height may be varied somewhat, for example in the range of about 7 feet to 8 feet above the floor. The lowered height of the ceiling structure 402 has advantages in providing a better focal length for the lighting of the OR/intervention room, as discussed more fully below, and requiring a shorter distance for the ventilation air to flow from the ceiling structure to the floor and then out of the OR/intervention room 400.

As previously mentioned, in conventional OR/surgical sites, lights are mounted on booms directly over the surgical site. These lights must be positioned manually by the surgeon or scrub nurse. Also, the suspended lights and boom obstruct the work zone. In addition, the lights and their support beams dramatically disrupt laminar flow of the ventilation air. Further, particulates and squames collect on the lights and the support beams, including during the time that the OR/surgical site is not in use, and then are drawn into the surgical site by the laminar ventilation flow. These drawbacks are substantially reduced, or even eliminated, by the OR/intervention room 400 and drop-down ceiling 402 that promote laminar air flow for the entire distance from the ceiling, to the surgical site, and then to the floor.

Also, the typical ten-plus-foot high ceilings in existing OR/surgical sites (necessitated by surgical light beams) enable cold air from the ceiling to accelerate in the downward air flow direction due to gravity. Air supplied at 30 feet per minute at the ceiling can accelerate to 90 feet per minute at the surgical site. This relatively high velocity air can overcome the "thermal plume" from the surgical wound and impinge contaminated particles into the wound site.

Also, the heat disseminated from typical surgical lights can cause the surgical staff to require lower ambient room temperatures for their comfort. For example, the supply air at the ceiling can be from about 5 to 15 degrees cooler than the ambient temperature. The requirement for lower ambient temperature due to heat from typical surgical lights, and the increase in laminar air flow velocity due to the ten-foot-plus high ceiling, can create a condition of hypothermia at the wound site. It has been documented that achieving nomothermia at a wound site can enhance healing and reduce the risk of surgical site infections. Thus, laminar air flow systems in typical OR/surgical sites can result in less than optimal conditions and may contribute to increased risk of surgical site infections.

The OR/intervention room 400 with its drop-down ceiling structure 402 also leads to "reduced age" of the air for the entire OR/intervention room generally, and also at the surgical site. Studies have shown that the age of the air in the OR/intervention room 400 is about 16% less than in a typical OR room with 10-foot-plus high ceilings. This reduced length of time air remains in the OR/intervention room 400 reduces the likelihood that the air is simply recirculating in the OR. It also reduces the possibility that the air at the surgical site comes from entrainment.

The drop-down ceiling structure 402 includes a perimeter sub-substructure 404 that defines the outer perimeter of the ceiling structure. A support grid 406 (see FIGS. 22 and 23) is supported by the lower portion of the perimeter substructure 404 which in turn supports a diffuser in the form of a perforated stainless steel ceiling panel 408. The support grid may be composed of inverted "T" members or structural members of other shapes. The ceiling panel 408 serves as a laminar airflow diffuser so that the uniform, laminar flow of ventilation air is supplied to and flows downwardly through the surgical zone. This uniform laminar air flow system reduces, or even substantially eliminates, any dead air spaces or air flow eddies that commonly occur in conventional OR/surgical rooms.

Figure 23:
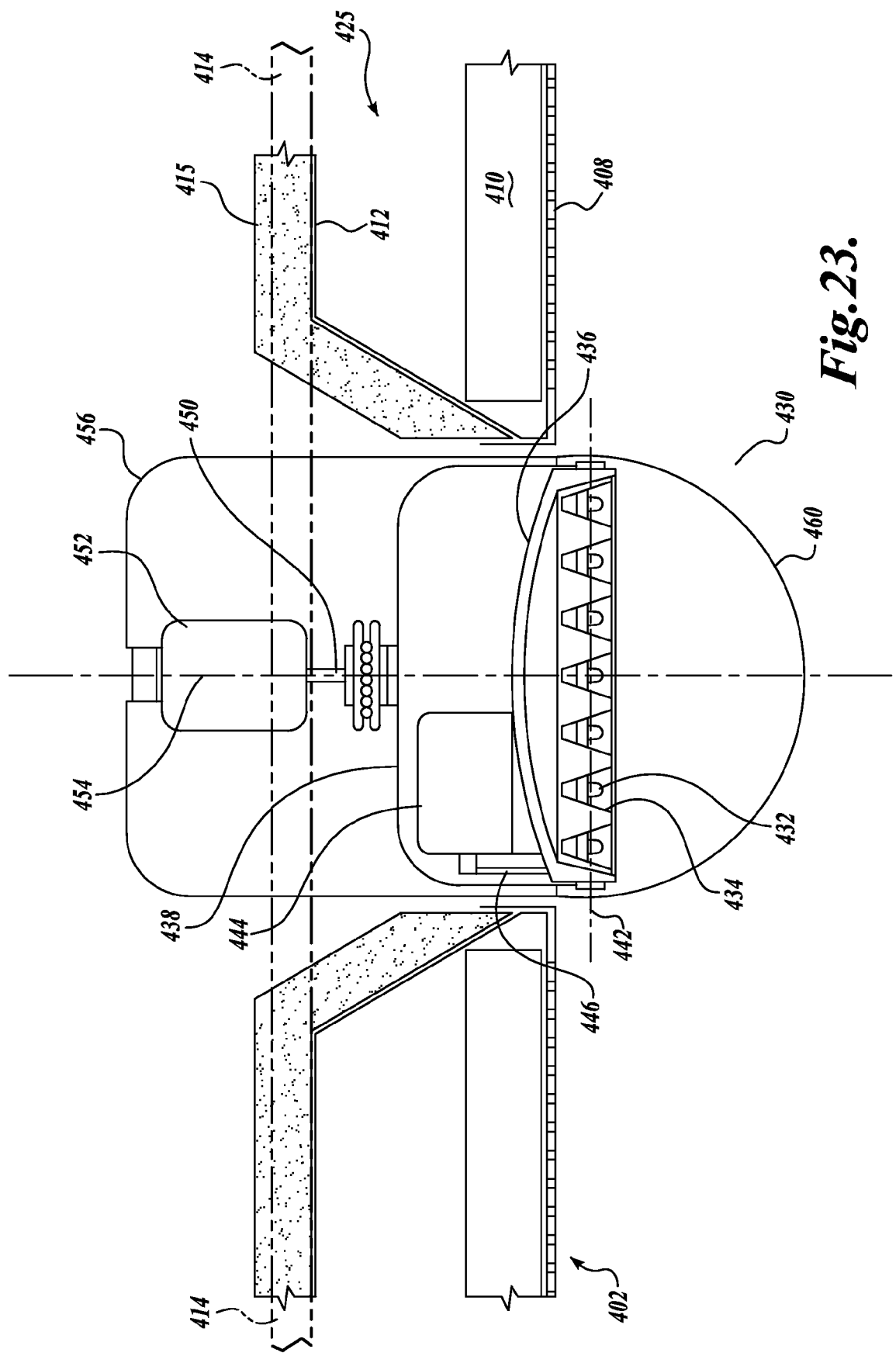
FIG. 23 is a side elevational view of one of the controllable light assemblies utilized in the drop-down ceiling of FIGS. 18-21.
Figure 24:
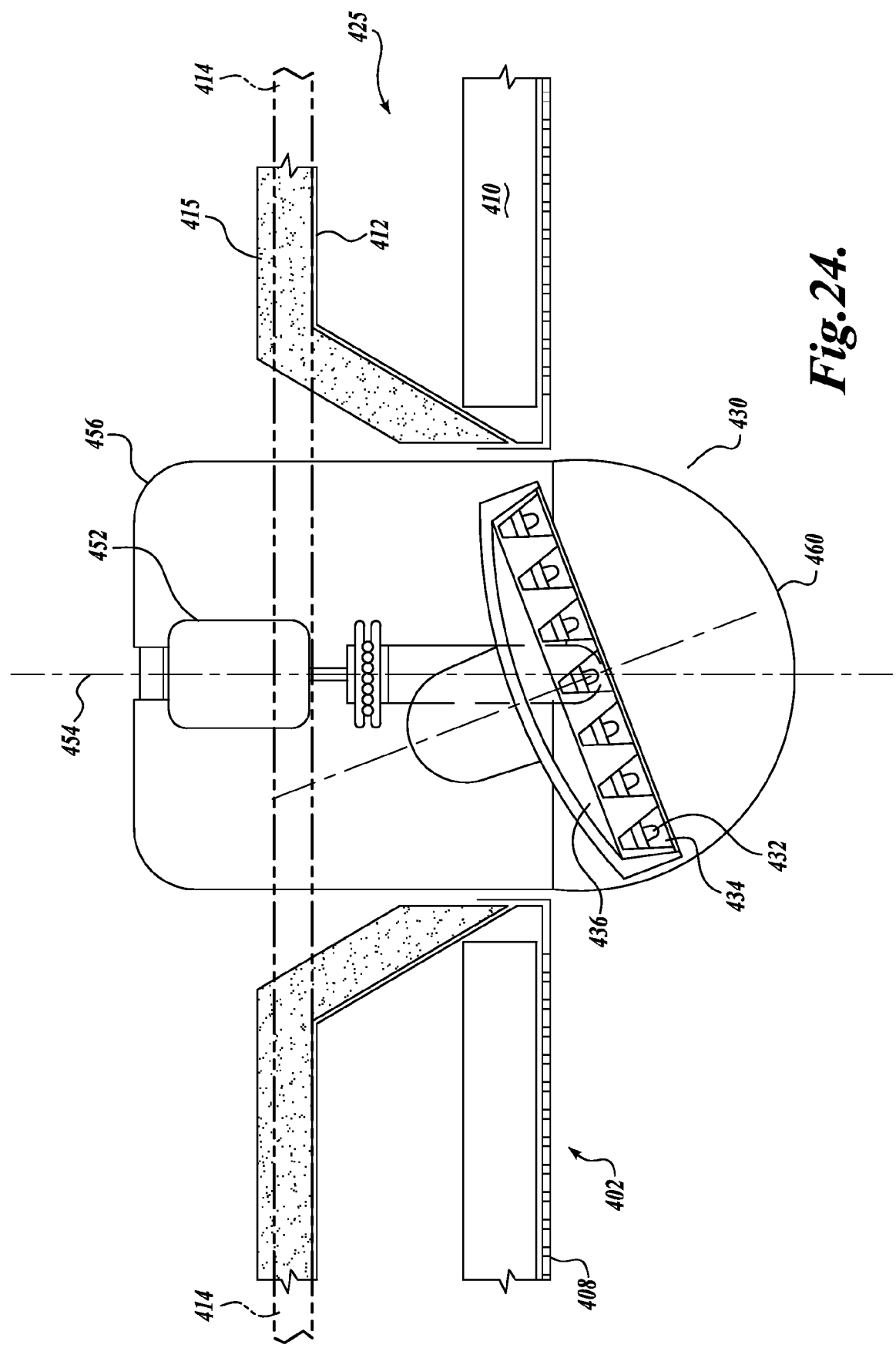
FIG. 24 is a view similar to FIG. 23, showing the light assembly tilted at an angle.

The perforated ceiling panel diffuser 408 supports a HEPA or other type of filter 410, see FIGS. 23 and 24. Of course, the HEPA filters may be alternatively located upstream. The ceiling structure also includes a diffuser housing 425 spaced above the diffuser in the form of panel 408). An insulation layer 414 overlies the upper panel 412 of the diffuser housing 424. The insulation layer can be composed of an appropriate material for heat and noise insulation. The ceiling structure is supported by a series of spaced apart support beams 415 that span across the ceiling 402 of the OR/intervention room, see FIG. 20. The beams 415 can be composed of structural channels, I beams or numerous other structural shapes and types that are sufficient to support the ceiling structure.

Referring specifically to FIG. 20, ventilation air for the OR/intervention room 400 is supplied from a building source to large ducts 420. The ducts 420 are attached to the building source ducts by a "quick connect" coupling apparatus pre-installed on both components for convenient and rapid installation. A series of branch distribution ducts 422 direct the ventilation air from ducts 420 downwardly and exhaust the ventilation air through volume control dampers 423 and old exhaust nozzles 424 at a location above ceiling diffuser panel 408. The distribution ducts 422 are arranged about the area of the diffuser 408 to provide substantially uniform flow of laminar air downwardly through the surgical site. Of course the volume, temperature, and other aspects of the air can be automatically or manually or semi-automatically controlled. As noted above, the reduced height of the ceiling structure 402 results in a shorter distance that the ventilation air flows from diffuser housing 424 and diffuser 408 to the floor, thereby enhancing the ability to provide laminar air flow through the surgical zone than if the air were required to flow downwardly from the full height of the OR/intervention room, typically at least 10 feet.

Figure 21:
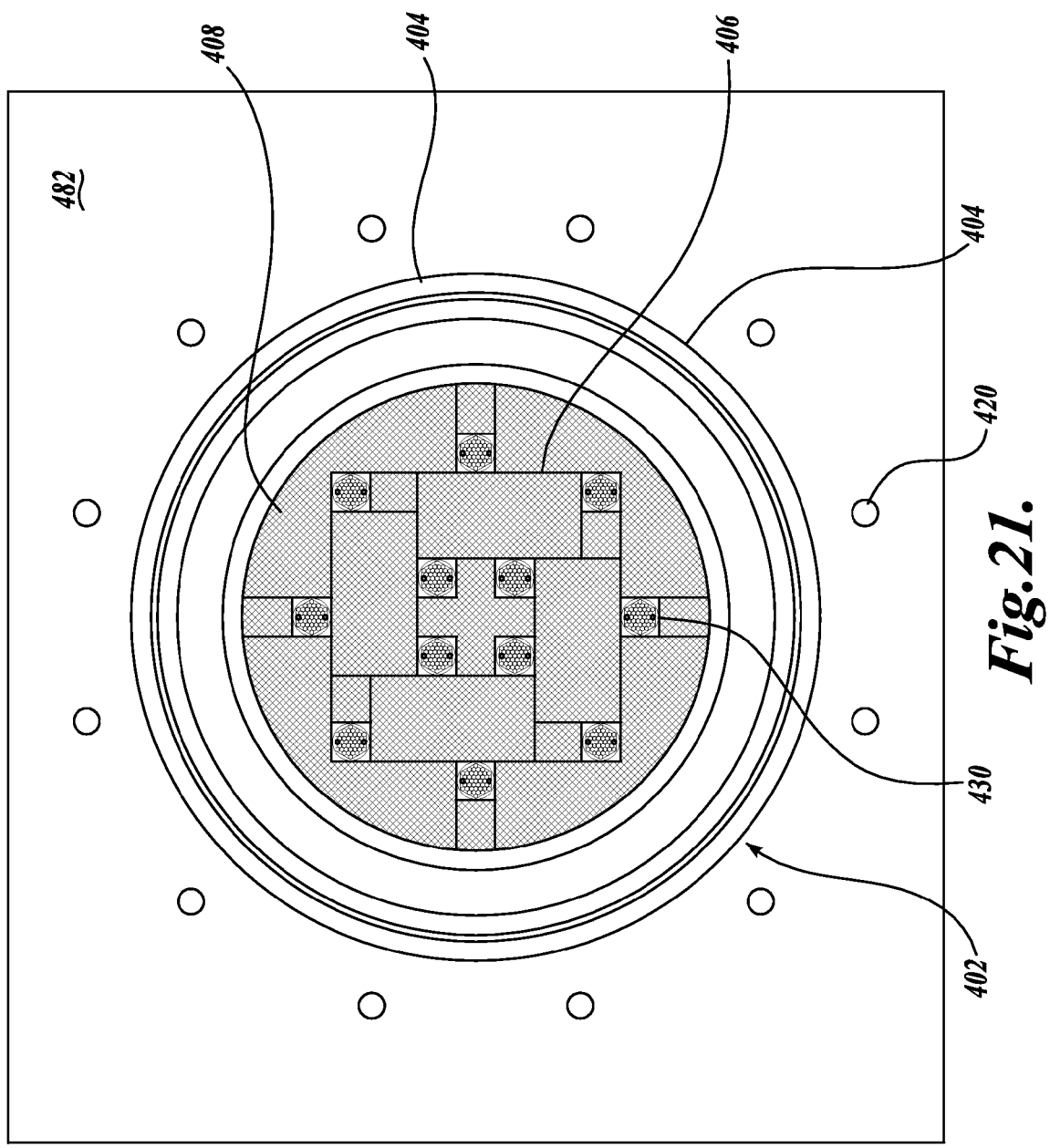
FIG. 21 is a view of the drop-down ceiling portion of FIGS. 18-20, looking upward from below.
Figure 22:
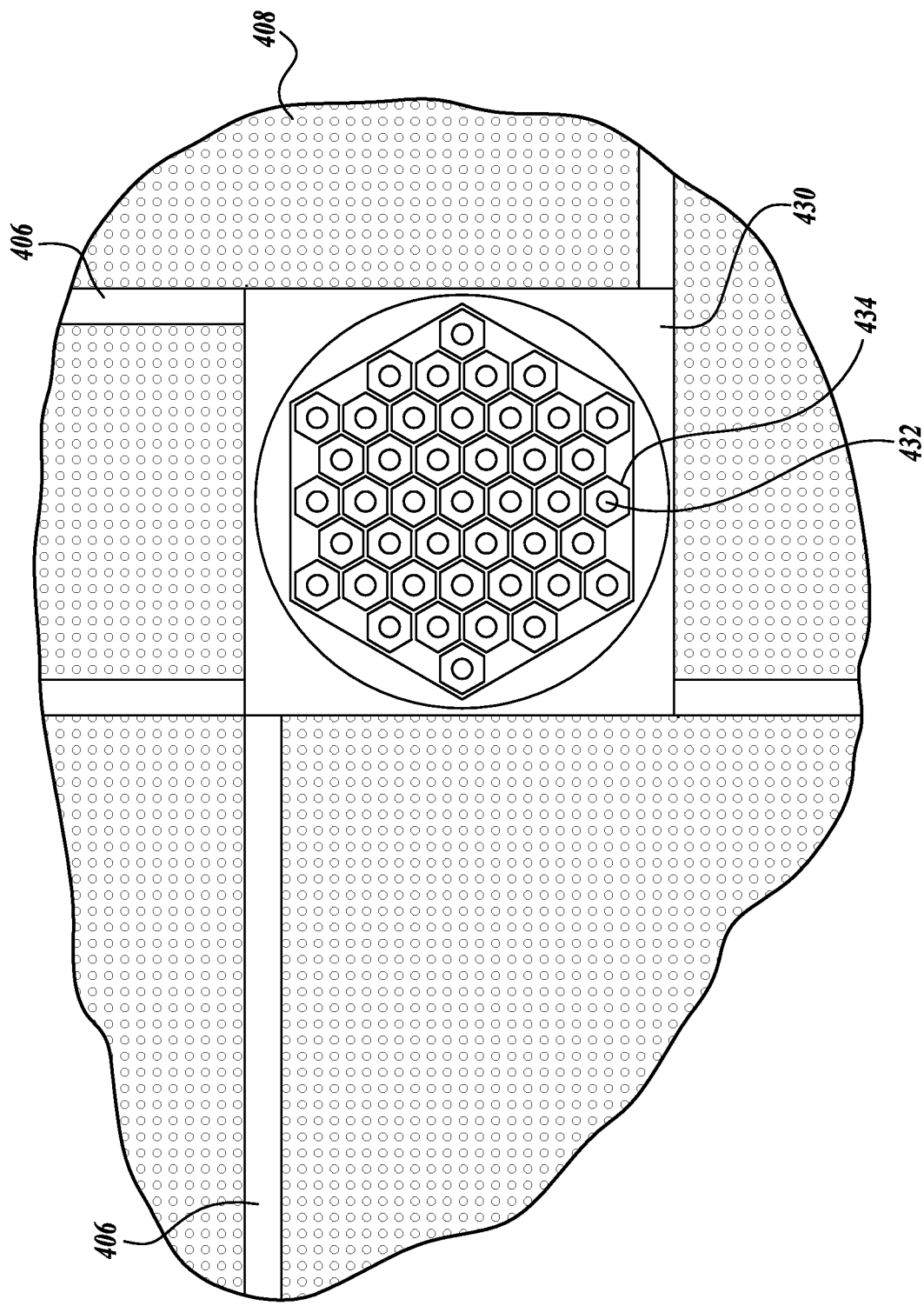
FIG. 22 is an enlarged, fragmentary view of FIG. 21.

Referring additionally to FIGS. 21-23, the series of light assemblies 430 are spaced about the area of ceiling panel 408. Several light assemblies 430 are clustered about the central portion of the ceiling panel to provide increased light at the surgical/operational site. The lights may be of various constructions. In FIGS. 22-24, such lights are shown as composed of an array of LED lights 432, each having a high performance reflector 434. The lights 432 and corresponding reflectors 434 are mounted on a carrier 436, which in turn is mounted on a yoke 438 to pivot about pivot axis 442. A servomotor 444 acts through a linkage assembly 446 to pivot the carrier 436, and thus lights 432, about axis 442.

The yoke 438 is in turn carried by a shaft 450, which may be rotated by a second servomotor 452, thereby to rotate the yoke about axis 454. The servometer 452 is mounted to and carried by a housing 456 constructed from perforated aluminum or other suitable material that can serve to mount the light assembly 430 rigidly to ceiling structure 402 and provide ventilation to remove the heat generated by the lights 432. As noted above, such removal of the heat from the lights can significantly improve the thermal conditions in the OR/intervention room 400. Rather than perforations, other types of ventilation openings can be used. Through the operation of the two servomotors 444 and 452, the lights 432 may be pivoted about a dual axis to enable the lights to be aimed at a desired direction, see FIG. 24.

A combination optical lens and dust-proof cover 460 is generally semi-circular in shape to cover the lights 432 as well as provide a desired directionality and focal length for the lights. The cover 460 mates with the housing 456 to protect and encase the internal components of the light assemblies 430 described above. As noted above, the drop-down ceiling structure 402 places the light assemblies 430 closer to the operational site than if the light assemblies were positioned at a higher elevation, as in present typical operating rooms for example, the elevation of ambient lights 470, as shown in FIG. 18.

The intensity and direction of lights 432 can be individually controlled or controlled in groups or collectively controlled to not only aim the light in desired direction(s), but also change the intensity and color temperature of the of the LED lights. Such control can be carried out by systems described above, including microchip-driven radio frequency controls, controls positioned in or on the glove of surgical/intervention room personnel, on a wrist band or head bank worn by surgical/intervention room personnel, or controlled by voice actuation. In addition, as described above, the controls for lights 432 can be tied to a radio frequency identification device or tag that can be imbedded in or mounted on a surgical tool or other device, located within the surgical/intervention zone, that would remain in static position during the procedure being conducted. Also, the lights can be pre-set by an automatic lighting system based on the procedure being performed. In this regard, the positioning of lights can be programmed using a wall panel or a remote control unit, or controlled from a central computer system or controlled by voice actuation.

The OR/intervention room 400, as in the other OR/intervention rooms of the present disclosure, includes a support ring or rail system 480 formed in the ceiling 482 of the room, see FIGS. 18 and 20. As in the rail system 180 discussed above, arm assemblies 484 extend downwardly from the rail system to support previously floor-mounted cabinets 486, tables, equipment, etc. The arm assembly 484 may be constructed to telescope upwardly and downwardly, and also includes articulating horizontal arms to move the cabinet 486 closer or further from the center of the surgical zone. Such movement can be controlled by remote-controlled device, including by voice actuation. As shown in FIGS. 18 and 20, additional arm structures 488 are provided for mounting monitors 490. The arm structure 488 is illustrated as being telescopically extendable downwardly or retractable upwardly. The monitor 490 could be mounted on other types of arm assemblies, including arm assembly 484, or arm assemblies described above and illustrated in other figures of the present disclosure. The rail system 440 also may be used to support a utility supply system, such as similar to system 210 shown in FIG. 14.

Although the drop-down ceiling structure is shown as circular in shape, it can be of other shapes, such as oval, triangular, square, or rectangular. Also, the drop-down ceiling structure and the associated lighting, ventilation, and other components described above can be pre-manufactured in an off site factory environment and subsequently installed in the OR/intervention room 400 as substantially a unitary product. For example, the unitary ceiling structure 402 can be designed to be attached to ceiling beams 414 by any number of standard attachment methods, such as by bolting or 5 welding.

The foregoing has described a number of advances in the structure, construction and usage of hospital/clinical facilities for performing of surgery interventions. It is to be understood that some or all of the foregoing advancements can be utilized in a particular situation. Also, although specific examples of the foregoing structures, apparatus and 10 methods have been described, the present invention is not limited thereto.

While illustrative embodiments have been illustrated and described, it will be appreciated that various changes can be made therein without departing from the spirit and scope of the invention.

The embodiments of the invention in which an exclusive property or privilege is claimed are defined as follows:

1. A pre-constructed, standalone, drop-down ceiling assembly for a medical facility operating/intervention room, comprising:
    a. a drop-down ceiling structure adapted for installation as a unit with a ceiling substrate of a medical facility operating/intervention room, said ceiling structure comprising a downwardly recessed sub-structure at an elevation below the substrate ceiling;
    b. a lighting system installed in the drop-down ceiling structure, said lighting system comprising:
        multiple light sources recessed into the recessed ceiling sub-structure;
        movable mounting systems for the light sources positioned within the recessed ceiling sub-structure; and
        a powered actuating system for moving the light mounting systems to aim the lights from the light sources as desired by operating/intervention room personnel; and
    c. a ventilation distribution system installed in the drop-down ceiling structure, said ventilation distribution system comprising a plurality of laminar flow outlets in the recessed ceiling sub-structure wherein ventilation air is able to travel from said outlets in a laminar flow condition from the drop-down ceiling sub-structure to the surgical site.

2. The pre-constructed, standalone, drop-down ceiling assembly of claim 1, wherein said drop-down ceiling structure further comprises a perimeter sub-structure that defines the outer perimeter of the drop-down ceiling structure.

3. The pre-constructed, standalone, drop-down ceiling structure of claim 2, wherein said perimeter sub-structure is adapted to be attachable to the substrate ceiling.

4. The pre-constructed, standalone, drop-down ceiling assembly of claim 1, wherein the recessed ceiling sub-structure is positionable over a surgical/intervention zone from about 7 feet to 8 feet from the floor.

5. The pre-constructed, standalone, drop-down ceiling assembly of claim 1, wherein the movable mounting systems of the lighting system are independently movable about first and second axes disposed transversely to each other.

6. The pre-constructed, standalone, drop-down ceiling assembly of claim 5, wherein the lighting system, comprising:
    a. an array of LED lights mounted on a carrier, said carrier rotatably connected to a support yoke adapted to rotate about the first axis relative to the support yoke; and
    b. a support shaft supporting the support yoke for rotation about said second axis.

7. The pre-constructed, standalone, drop-down ceiling assembly of claim 1, wherein the lighting system further comprising a control system for controlling the powered actuating system and for controlling the intensity of the light sources.

8. The pre-constructed, standalone, drop-down ceiling assembly of claim 1, wherein the laminar flow outlets of the ventilation distribution system correspond with a plurality of air exhaust systems adjacent the floor of the operating/intervention room, whereby ventilation air is able to travel in a laminar flow condition from the outlets of the recessed ceiling sub-structure to the surgical site and then to the floor exhaust system.

9. A pre-constructed, drop-down ceiling assembly mountable as a standalone unit in the ceiling of an operating/intervention room to define and extend over a surgical/intervention zone of a predetermined area generally surrounding the location where a patient is positionable, comprising:
    a. a drop-down ceiling structure extending downwardly from the ceiling height of the rest of the operating/intervention room;
    b. a lighting system pre-constructed into the ceiling structure; and
    c. a ventilation distribution system pre-constructed with the drop-down ceiling structure.

10. The pre-constructed, drop-down ceiling assembly of claim 9, wherein said drop-down ceiling structure extending downwardly from the ceiling height of the rest of the operating/intervention room to a position of between 7 and 8 feet from the floor.

11. The pre-constructed, drop-down ceiling assembly according to claim 9, wherein said drop-down ceiling structure comprising a perimeter structure defining the outer perimeter of the drop-down ceiling structure.

12. The pre-constructed, drop-down ceiling assembly of claim 11, wherein the perimeter structure is adapted for mounting the drop-down ceiling assembly to the operating/intervention room ceiling.

13. The pre-constructed, drop-down ceiling assembly according to claim 9, wherein the lighting system comprising:
    a. multiple light sources recessed into the drop-down ceiling structure;
    b. movable mounting systems for the light sources positioned within the drop-down ceiling structure; and
    c. a powered actuating system for moving the light mounting systems to aim the lights from the light sources as desired by operating/intervention room personnel.

14. The pre-constructed, drop-down ceiling assembly according to claim 13, wherein the lighting system further comprising a control system for controlling the powered actuating system and for controlling the intensity of the light sources.

15. The pre-constructed, drop-down ceiling assembly according to claim 13, wherein the movable mounting systems of the lighting system are independently movable about first and second axes disposed transversely to each other.

16. The pre-constructed, drop-down ceiling assembly according to claim 15, wherein the lighting system comprising:
    a. an array of LED lights mounted on a carrier, said carrier rotatably connected to a support yoke adapted to rotate about the first axis relative to the support yoke; and
    b. a support shaft mounting the support yoke for rotation about the second axis.

17. The pre-constructed, drop-down ceiling assembly according to claim 9, wherein the ventilation system comprising a plurality of laminar flow outlets in the drop-down ceiling structure, whereby ventilation air is able to travel from the outlets in a laminar flow condition to the surgical site.

18. The pre-constructed, drop-down ceiling assembly according to claim 17, wherein the ventilation system includes a plurality of air exhaust systems adjacent the floor of the operating/intervention room, whereby ventilation air is able to travel in laminar flow condition from the outlets of the drop-down ceiling structure to the surgical site and then to the floor exhaust system.

* * * * *